US007092825B1

(12) United States Patent
Smythe et al.

(10) Patent No.: US 7,092,825 B1
(45) Date of Patent: Aug. 15, 2006

(54) PROTEIN ENGINEERING

(75) Inventors: Mark Leslie Smythe, Bardon (AU); Michael John Dooley, Kenmore (AU); Peter Ronald Andrews, St. Lucia (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 09/830,011

(22) PCT Filed: Oct. 21, 1999

(86) PCT No.: PCT/AU99/00914

§ 371 (c)(1),
(2), (4) Date: Jul. 23, 2001

(87) PCT Pub. No.: WO00/23474

PCT Pub. Date: Apr. 27, 2000

(30) Foreign Application Priority Data

Oct. 21, 1998 (AU) .................................... PP6606

(51) Int. Cl.
*G06F 9/455* (2006.01)
*G06F 17/30* (2006.01)
*C07K 14/00* (2006.01)

(52) U.S. Cl. .......................... 702/19; 530/300; 702/27

(58) Field of Classification Search .................. 702/19, 702/27, 150, 151, 152, 153
See application file for complete search history.

(56) References Cited

U.S. PATENT DOCUMENTS 4,853,871 A * 8/1989 Pantoliano et al. ........... 701/99
5,643,564 A * 7/1997 Hamaguchi et al. ....... 424/85.1
5,752,019 A 5/1998 Rigoutsos et al. .......... 395/603

FOREIGN PATENT DOCUMENTS

EP 0 936 565 8/1999
WO 94/18232 8/1994
WO 97/41526 11/1997
WO 99/22019 5/1999

OTHER PUBLICATIONS

Lauri et al. Journal of Computer Aided Molecular Design, vol. 8 (1994) pp. 51-66.*

Derwent Abstract Accession No. 87-327750/46, "Computer Based Method For Converting Chain Polypeptide Comparing Three Dimensional Vector From Tail To Head Of Candidate, to Vector From Tail To Head of Gap",, (Nov. 1987).

Derwent Abstract Accession No. 93-045645/05, "Characterising The Three-Dimensional Structure Of A Protein By Analysing Aminoacid Residue Positions And Comparing With Know Protein Structures", (Jan. 1993).

Derwent Abstract Accession No. 99-213438/18, Determination Of Three-Dimensional Structure Of Protein Sequences, (Mar. 1999).

Derwent Abstract Accession No. 94-128835/16, Indicatio nof SS Bond In Protein Having Stereo Configuration, (Mar. 1994).

Derwent Abstract Accession No. 99-264101/22, Method For Inferring Three-Dimensional protein Structure, Useful in Providing Information On Amino-Acid Sequences And Their Stereochemistry, Application e.g. In Drug Development, (Apr. 1999).

Derwent Abstract Accession No. 99-120378/10, "Inferring The Biological Function Of A Protein Using A Ligand Database", Jan. 1999).

Swiss-Prot Abstract Accessio nlD SCKL-LEIQH, Leiurotoxin I (LETX I (SCYLLATOXIN), Apr. 1, 1990.

Swiss-Prot Abstract Accession ID SCK5-ANDMA, "Leiurotoxin I-Like Toxin P05", Jul. 1, 1993.

* cited by examiner

*Primary Examiner*—Marjorie A. Moran
*Assistant Examiner*—Lori A. Clow
(74) *Attorney, Agent, or Firm*—Foley & Lardner LLP

(57) ABSTRACT

A method of protein engineering is provided wherein a searchable computer database is created comprising entries in the form of descriptions of a location and orientation in 3D space of side chains of the constituent amino acid residues of a framework protein. A query is created which corresponds to a description of a location and orientation in 3D space of respective side chains of amino acid residues of a sample protein. The location and orientation in 3D space of constituent side-chains is preferably described as a Cα–Cβ vector. The query is used to search the database and thereby identify a hit which corresponds to a framework protein having structural similarity with said sample protein. Framework protein "hits" so identified may be suitable candidates for further modification. A particular advantage of the present invention is that a modified framework protein may display one or more desired characteristics, such as a function similar to or inhibitory of the sample protein.

13 Claims, 14 Drawing Sheets

Figure 1:
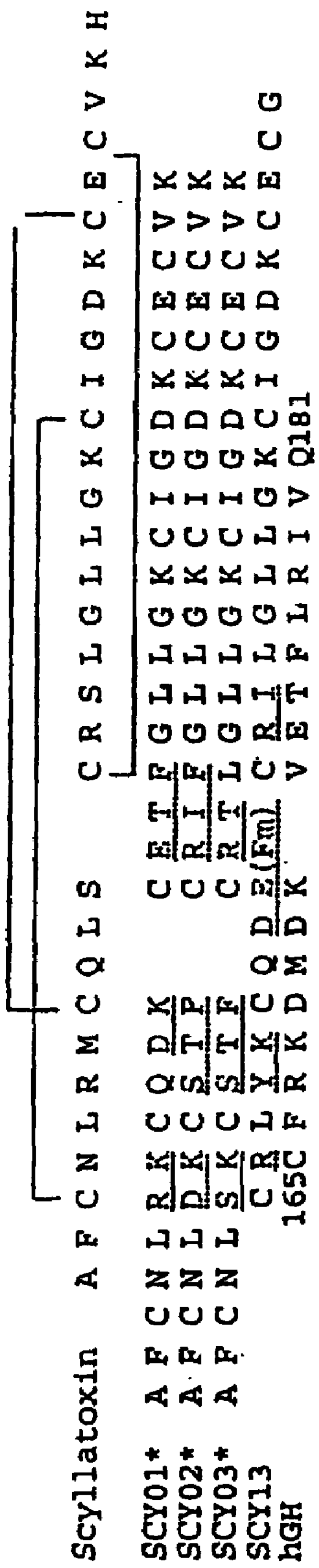

```
VIB Native  A C E N N C R K K Y D L C I R C Q G K W A G K R G K C A A H C I T Q K N N C K G K C K K E
VIB01       A C R K D C D K K E T F C I R C Q G K E A G K D G N C A A R C I R L H Q L C F G K C A K E
hGH         65C F R K D M D K V E T F L R I V Q181 - N A M L R A H R L H Q L A F D26
```

Overlay of pdb1scy and GH-SCY0

GH-SCY01

Pdb1scy

```
ZDC                 F N M Q C Q R R F Y E A L H D P N L N E E Q R N A K I K S I R D D C
ZDC05               F N Y D C Q K D F E E G L Q T P G L N E E R R N D N I K L R R D R C
hGH     105A S D S N V Y D L L K D L E E G I Q T123
hGH                                          1F P T I P L S R L F D N A M L R A H R L H21
```

FIG. 9

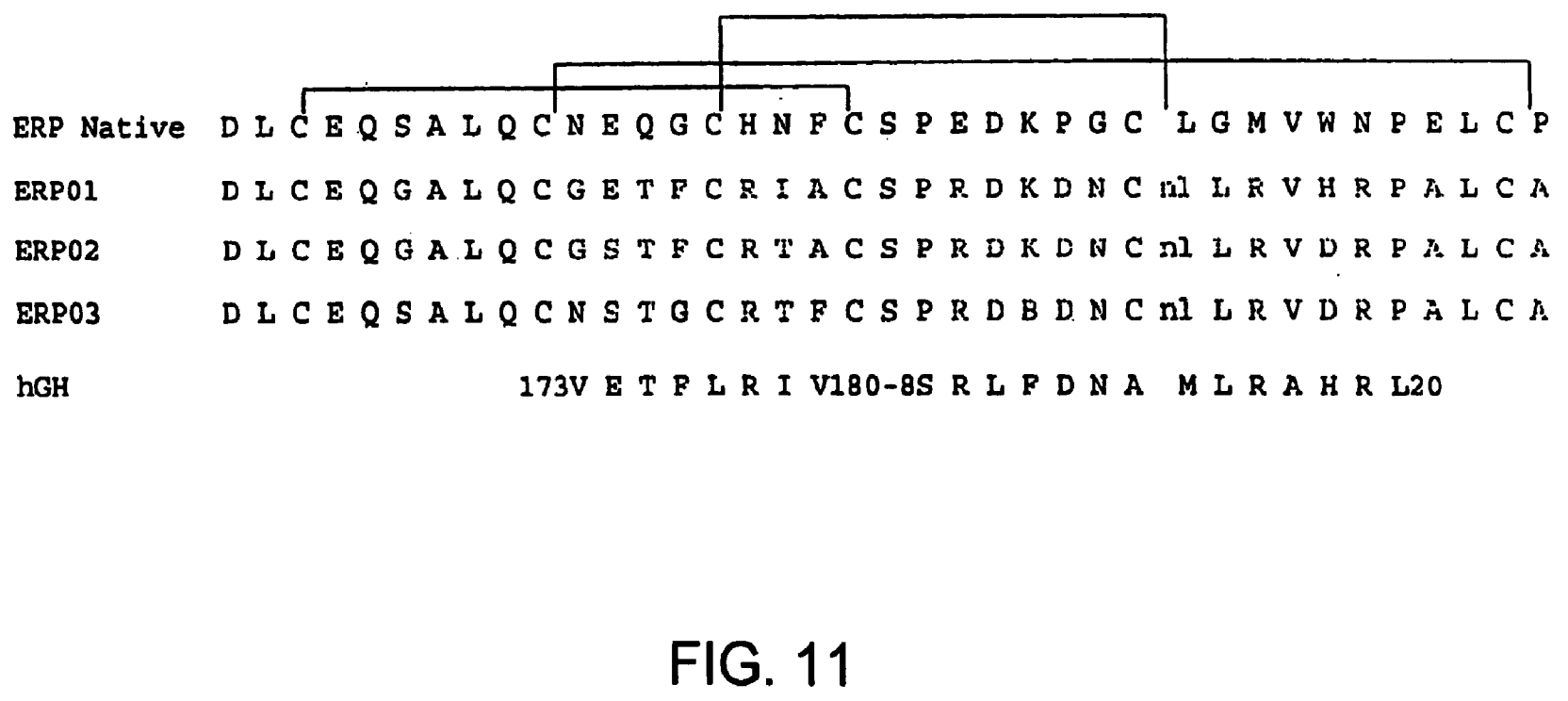

```
ERP Native  D L C E Q S A L Q C N E Q G C H N F C S P E D K P G C    L G M V W N P E L C P
ERP01       D L C E Q G A L Q C G E T F C R I A C S P R D K D N C nl L R V H R P A L C A
ERP02       D L C E Q G A L Q C G S T F C R T A C S P R D K D N C nl L R V D R P A L C A
ERP03       D L C E Q S A L Q C N S T G C R T F C S P R D B D N C nl L R V D R P A L C A
hGH                           173V E T F L R I V180-8S R L F D N A    M L R A H R L20
```

FIG. 11

SEQUENCE LISTING

```
<160> NUMBER OF SEQ ID NOS: 26

<210> SEQ ID NO 1
<211> LENGTH: 31
<212> TYPE: PRT
<213> ORGANISM: Leiurus quinquestriatus

<400> SEQUENCE: 1

Ala Phe Cys Asn Leu Arg Met Cys Gln Leu Ser Cys Arg Ser Leu Gly
  1               5                  10                  15

Leu Leu Gly Lys Cys Ile Gly Asp Lys Cys Glu Cys Val Lys His
             20                  25                  30


<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Phe Cys Asn Leu Arg Lys Cys Gln Asp Lys Cys Glu Thr Phe Gly
  1               5                  10                  15

Leu Leu Gly Lys Cys Ile Gly Asp Lys Cys Glu Cys Val Lys
             20                  25                  30


<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Phe Cys Asn Leu Asp Lys Cys Ser Thr Phe Cys Arg Ile Phe Gly
  1               5                  10                  15

Leu Leu Gly Lys Cys Ile Gly Asp Lys Cys Glu Cys Val Lys
```

-continued

```
            20                  25                  30


<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Phe Cys Asn Leu Ser Lys Cys Ser Thr Phe Cys Arg Thr Leu Gly
  1               5                  10                  15

Leu Leu Gly Lys Cys Ile Gly Asp Lys Cys Glu Cys Val Lys
            20                  25                  30


<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Arg Leu Tyr Lys Cys Gln Asp Glu Cys Arg Ile Leu Gly Leu Leu
  1               5                  10                  15

Gly Lys Cys Ile Gly Asp Lys Cys Glu Cys Gly
            20                  25


<210> SEQ ID NO 6
<211> LENGTH: 17
<212> TYPE: PRT
<213> ORGANISM: Homo sapiens

<400> SEQUENCE: 6

Cys Phe Arg Lys Asp Met Asp Lys Val Glu Thr Phe Leu Arg Ile Val
  1               5                  10                  15

Gln


<210> SEQ ID NO 7
<211> LENGTH: 45
<212> TYPE: PRT
<213> ORGANISM: Cerebratulus lacteus

<400> SEQUENCE: 7

Ala Cys Glu Asn Asn Cys Arg Lys Lys Tyr Asp Leu Cys Ile Arg Cys
  1               5                  10                  15

Gln Gly Lys Trp Ala Gly Lys Arg Gly Lys Cys Ala Ala His Cys Ile
            20                  25                  30

Ile Gln Lys Asn Asn Cys Lys Gly Lys Cys Lys Lys Glu
        35                  40                  45


<210> SEQ ID NO 8
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Cys Arg Lys Asp Cys Asp Lys Lys Glu Thr Phe Cys Ile Arg Cys
  1               5                  10                  15
```

-continued

Gln Gly Lys Phe Ala Gly Lys Asp Gly Asn Cys Ala Ala Arg Cys Ile
20 25 30

Arg Leu His Gln Leu Cys Phe Gly Lys Cys Ala Lys Glu
35 40 45

<210> SEQ ID NO 9
<211> LENGTH: 17
<212> TYPE: PRT
<213> ORGANISM: Homo sapiens

<400> SEQUENCE: 9

Cys Phe Arg Lys Asp Met Asp Lys Val Glu Thr Phe Leu Arg Ile Val
1 5 10 15

Gln

<210> SEQ ID NO 10
<211> LENGTH: 16
<212> TYPE: PRT
<213> ORGANISM: Homo sapiens

<400> SEQUENCE: 10

Asp Asn Ala Met Leu Arg Ala His Arg Leu His Gln Leu Ala Phe Asp
1 5 10 15

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Phe Asn Met Gln Cys Gln Arg Arg Phe Tyr Glu Ala Leu His Asp Pro
1 5 10 15

Asn Leu Asn Glu Glu Gln Arg Asn Ala Lys Ile Lys Ser Ile Arg Asp
20 25 30

Asp Cys

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Phe Asn Tyr Asp Cys Gln Lys Asp Phe Glu Glu Gly Leu Gln Thr Pro
1 5 10 15

Gly Leu Asn Glu Glu Arg Arg Asn Asp Asn Ile Lys Leu Arg Arg Asp
20 25 30

Arg Cys

<210> SEQ ID NO 13
<211> LENGTH: 19
<212> TYPE: PRT
<213> ORGANISM: Homo sapiens

<400> SEQUENCE: 13

Ala Ser Asp Ser Asn Val Tyr Asp Leu Leu Lys Asp Leu Glu Glu Gly
1 5 10 15

-continued

```
Ile Gln Thr


<210> SEQ ID NO 14
<211> LENGTH: 21
<212> TYPE: PRT
<213> ORGANISM: Homo sapiens

<400> SEQUENCE: 14

Phe Pro Thr Ile Pro Leu Ser Arg Leu Phe Asp Asn Ala Met Leu Arg
  1               5                  10                  15

Ala His Arg Leu His
             20


<210> SEQ ID NO 15
<211> LENGTH: 38
<212> TYPE: PRT
<213> ORGANISM: Euplotes raikovi

<400> SEQUENCE: 15

Asp Leu Cys Glu Gln Ser Ala Leu Gln Cys Asn Glu Gln Gly Cys His
  1               5                  10                  15

Asn Phe Cys Ser Pro Glu Asp Lys Pro Gly Cys Leu Gly Met Val Trp
             20                  25                  30

Asn Pro Glu Leu Cys Pro
         35


<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)
<223> OTHER INFORMATION: Norleucine

<400> SEQUENCE: 16

Asp Leu Cys Glu Gln Gly Ala Leu Gln Cys Gly Glu Thr Phe Cys Arg
  1               5                  10                  15

Ile Ala Cys Ser Pro Arg Asp Lys Asp Asn Cys Xaa Leu Arg Val His
             20                  25                  30

Arg Pro Ala Leu Cys Ala
         35


<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)
<223> OTHER INFORMATION: Norleucine

<400> SEQUENCE: 17

Asp Leu Cys Glu Gln Gly Ala Leu Gln Cys Gly Ser Thr Phe Cys Arg
  1               5                  10                  15

Thr Ala Cys Ser Pro Arg Asp Lys Asp Asn Cys Xaa Leu Arg Val Asp
             20                  25                  30
```

-continued

```
Arg Pro Ala Leu Cys Ala
        35


<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)
<223> OTHER INFORMATION: Norleucine

<400> SEQUENCE: 18

Asp Leu Cys Glu Gln Ser Ala Leu Gln Cys Asn Ser Thr Gly Cys Arg
  1               5                  10                  15

Thr Phe Cys Ser Pro Arg Asp Asx Asp Asn Cys Xaa Leu Arg Val Asp
             20                  25                  30

Arg Pro Ala Leu Cys Ala
        35


<210> SEQ ID NO 19
<211> LENGTH: 8
<212> TYPE: PRT
<213> ORGANISM: Homo sapiens

<400> SEQUENCE: 19

Val Glu Thr Phe Leu Arg Ile Val
  1               5


<210> SEQ ID NO 20
<211> LENGTH: 14
<212> TYPE: PRT
<213> ORGANISM: Homo sapiens

<400> SEQUENCE: 20

Ser Arg Leu Phe Asp Asn Ala Met Leu Arg Ala His Arg Leu
  1               5                  10


<210> SEQ ID NO 21
<211> LENGTH: 35
<212> TYPE: PRT
<213> ORGANISM: Homo sapiens

<400> SEQUENCE: 21

Thr Ile Ser Cys Thr Asn Pro Lys Gln Cys Tyr Pro His Cys Lys Lys
  1               5                  10                  15

Glu Thr Gly Tyr Pro Asn Ala Lys Cys Met Asn Arg Lys Cys Lys Cys
             20                  25                  30

Phe Gly Arg
        35


<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Cys Ser Asn Pro Lys Gln Cys Tyr Pro His Cys Lys Lys Glu Thr
  1               5                  10                  15
```

-continued

```
Gly Tyr Pro Asn Ala Gly Cys Gln Gly Ser Phe Cys Thr Cys Lys Gly
            20                  25                  30


<210> SEQ ID NO 23
<211> LENGTH: 31
<212> TYPE: PRT
<213> ORGANISM: Leiurus quinquestriatus

<400> SEQUENCE: 23

Ala Phe Cys Asn Leu Arg Met Cys Gln Leu Ser Cys Arg Ser Leu Gly
  1               5                  10                  15

Leu Leu Gly Lys Cys Ile Gly Asp Lys Cys Glu Cys Val Lys His
            20                  25                  30


<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Asn Leu Ala Arg Cys Gln Leu Ser Cys Lys Ser Leu Gly Leu Lys
  1               5                  10                  15

Gly Gly Cys Gln Gly Ser Phe Cys Thr Cys Gly
            20                  25


<210> SEQ ID NO 25
<211> LENGTH: 13
<212> TYPE: PRT
<213> ORGANISM: Homo sapiens

<400> SEQUENCE: 25

Ile Leu Gly Asn Gln Gly Ser Phe Leu Thr Lys Gly Pro
  1               5                  10


<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ser Ser Gly
  1
```

PROTEIN ENGINEERING

This application is a 371 of PCT 09/00914 filed Oct. 21, 1999.

FIELD OF THE INVENTION

THIS INVENTION relates to a method of identifying proteins suitable for protein engineering. In particular, the present invention relates to a computer database searching method of identifying proteins according to aspects of three-dimensional structure, and furthermore to the modification of proteins so identified to thereby possess one or more desired characteristics. Although not limited thereto, this invention relates to engineered proteins such as cytokine mimetics.

BACKGROUND OF THE INVENTION

Proteins are central to life due to their crucial involvement in a variety of biological processes, such as enzyme catalysis of biochemical reactions, control of nucleic acid transcription and replication, hormonal regulation, signal transduction cascades and antigen recognition during immune responses.

In many cases, one or more structural regions of a protein are responsible for a particular function, hereinafter referred to as "functional regions". These regions may constitute the active site of a protein enzyme, the nucleic acid binding domain of a transcription factor, a region of a protein cytokine crucial to binding the specific receptor for that cytokine, or antigen-binding regions of antigen receptors.

A functional region of a protein usually comprises one or more amino acids which are required for that particular function, that is, they are essential for that function.

In many cases, although these required amino acid residues are topographically proximal to each other, they may be well separated with respect to primary amino acid sequence, that is, they are non-contiguous. In addition, where there is more than one functional region of a protein, these regions may also be topographically proximal, but well separated in terms of primary amino acid sequence. In some cases, however, where there is more than one functional region involved in a particular function, these functional regions may also be topographically well separated. This is a particularly important point with regard to the functional regions of cytokines.

"Cytokine" as used herein includes and encompasses soluble protein molecules which have a cognate cell surface receptor, and which are involved in initiating, controlling and otherwise regulating a variety of processes relevant to cell growth, death and differentiation. Cytokines are typically exemplified by interferons (e.g. IFN-γ), interleukins (for example IL-2, IL-4 and IL-6), growth and differentiation factors [e.g. granulocyte colony stimulating factor (G-CSF) and erythropoietin (EPO)] and others such as growth hormone (GH), prolactin, TGF-β, tumour necrosis factor (TNF) and insulin. Each of these molecules is capable of binding a specific receptor and thereby eliciting a particular biological response or set of responses.

The fact that a particular function of a protein can be attributed to one or more functional regions of that protein has formed the basis for strategies aimed at modifying a protein by adding or subtracting functional regions to modify the function of that protein.

In this regard, the design and engineering of cytokine mimetics has become an area of major importance, as many cytokine—cytokine receptor interactions are central to the regulation of a variety of biological processes. It is envisaged that new mimetics will therefore become important new therapeutic agents that either mimic or inhibit the biological response to cytokine—cytokine receptor interactions.

A "mimetic" is a molecule which elicits a biological response either similar to, or more powerful than, that of another molecule (an "agonist"), or inhibits the action of the other molecule (an "antagonist"). The other molecule may be a cytokine, for example.

With regard to designing and engineering mimetics based on cytokines, a problem frequently encountered with many engineered mimetics has been that they exhibit short biological half-lives and hence minimal bioavailability and efficacy. In this regard, it has been proposed that small cysteine-rich proteins might be useful as protein "scaffolds" as a basis for engineering mimetics, due to their stability (Vita et al., 1995, Proc. Natl. Acad. Sci. USA 92 6404). These small cysteine-rich proteins comprise a disulfide-bonded core and exposed amino acid side chains at the protein surface (Neilsen et al., 1996, J. Mol. Biol. 263 297). However the full potential of these proteins has not been realized due to the fact that typical prior art strategies for protein engineering have largely been limited to transferring or exchanging contiguous groups of amino acids within individual secondary structural elements, such as loops or helices or β-sheets and no design strategies exist for selecting the most appropriate disulfide-rich candidiate.

Examples of such an approach would include: the exchange of secondary structural regions between RNase and angiogenin, either to confer RNase activity on angiogenin (Harper et al., 1989, Biochemistry 28 1875) or angiogenic activity on RNase (Raines et al., 1995, J. Biol. Chem. 27017180); the insertion of elastase inhibition activity into IL-1β by transfer of the protease inhibitor loop of elastase to the IL-1β scaffold (Wolfson et al., 1993, Biochemistry 32 5327); the insertion of a 10 amino acid calcium-binding loop of thermolysin into *Bacillus subtilis* neutral protease (Toma et al., 1991, Biochemistry 30 97); the insertion of a β-sheet from a snake toxin to replace the β-sheet of charybdotoxin (Drakopolou et al., 1996, J. Biol. Chem. 271 11979); and the incorporation of a β-sheet from carbonic anhydrase into the β-sheet of charybdotoxin (Pierret et al., 1995, J. Med. Chem. 35 2145).

Of growing importance in protein engineering has been the use of computer based technology combined with the elucidation of the 3D structures of small molecules and macromolecules. 3D molecular structures are being generated at an increasing rate, such as by X-Ray crystallography and NMR techniques. These 3D features can be stored in generally accessible, searchable databases, such as the BROOKHAVEN database.

For the purposes of this specification, a database will comprise a collection of "entries", each entry corresponding to a representation of an aspect of 3D structure of a framework protein. A framework protein is simply any protein for which a 3D structure exists, either by experimental elucidation or by predictive means such as computer modelling. A framework protein is potentially useful as a scaffold which can be structurally modified for the purposes of imparting a particular function thereto.

A "query" refers herein to a representation of an aspect of 3D structure of a protein which exhibits a function of interest. The representation of 3D structure would be in a form suitable for searching a database with the intention of identifying a "hit". A hit is an entry identified according to the particular query and the algorithm used to perform the search.

An important advance in database searching has been made by representing 3D structures in terms of the relationship between atoms located in "distance space", rather than "Cartesian space" (Jakes & Willett, 1986, J. Mol. Graphics 4 12; Ho & Marshall, 1993, J. Comp. Aided. Mol. Des. 7 3). A location in Cartesian space is defined by three coordinates (x, y, z) which each correspond to a position along three respective axes (X, Y, Z), each axis being oriented at right angles to the other two.

A location in distance space, however, is defined by distances between atoms, expressed in the form of a distance matrix, which details the distance between atoms. Distance matrices are therefore coordinate independent, and comparisons between distance matrices can be made without restriction to a particular frame of reference, such as is required using Cartesian coordinates.

It is important to emphasise that an arrangement of atoms and its mirror image are described by identical distance matrices. A root mean squared (RMS) difference can be used to alleviate this ambiguity.

With regard to the 3D structure of proteins, a simplification of protein structure can be provided by reducing a 3D structure to "Cα–Cβ vectors" as discussed in McKie et al., 1995, Peptides: Chemistry, Structure & Biology p 354–355. A Cα–Cβ vector occupies a location in 3D space, the location being defined by the orientation of the covalent bond between the α carbon and β carbon atoms of an amino acid (Lauri & Bartlett, 1994, J. Comp. Aid. Mol. Des. 8 51). It will be appreciated that each of the 20 naturally-occurring constituent amino acids of a protein (except glycine), possess a Cα–Cβ vector due to the covalent bond between the "central" α carbon and the β carbon of the constituent side chain.

For those proteins containing Gly in the database, it is possible to mutate this to Ala to generate the required Cα–Cβ vector for database searching.

The usefulness of Cα–Cβ vectors is that they provide a simplification of 3D structure. Therefore, only the amino acid side-chains of a functional region of a protein need be represented by the Cα–Cβ vector map, thereby excluding the substantial portion of the protein(s) not directly involved in that particular function. For the purposes of database searching, Cα–Cβ vectors are ideal, as they constitute the basic 3D structural information needed.

After identification of Cα–Cβ vectors corresponding to a protein or a functional region thereof, the parameters that characterize each vector must be stored in a database in such a way that retrieval in response to a query can be made quickly. A number of options are available for suitable representation of Cα–Cβ vectors, whether as a database entry or as a query:—

(A) as a distance matrix;

(B) as a dihedral angle (δ) formed between respective Cα–Cβ vectors;

(C) as angles $\alpha_1$ and $\alpha_2$ formed between respective Cα–Cβ vectors.

A simple explanation of these representations is provided in Lauri & Bartlett, 1994, supra, which is hereinafter incorporated by reference. The key to successful database searching is speed and efficiency. Thus, computer search algorithms have been developed which use a strategy whereby the vast majority of entries in the database are eliminated in a preliminary screening step.

These algorithms are demanding of computer resources, and therefore a search is normally effected in two stages:—

(1) a screening search to eliminate entries that cannot possibly constitute a hit; and (2) an atom-by-atom comparison of a query with each entry not eliminated in (1), to identify one or more hits.

The search in (1) could screen entries based on geometric attributes of the query (Lesk, 1979, Commun. ACM 22 219) interatomic distances and atom types (Jakes & Willett, 1986, supra), aromaticity, hybridization, connectivity, charge, position of lone pair electrons, or centre of mass of ring structures (Sheridan et al., 1989, Proc. Natl. Acad. Sci. 86 8165). This screening process would eliminate entries that have no chance of meeting the 3D constraints of the query.

This strategy, although quick, requires that for an entry to register as a hit, it must comprise every specified query component. As the number of query components increases, the number of near misses increases and the likelihood of finding a hit decreases.

A more useful search strategy which assesses the relative merits of each near miss as well as each hit has recently been provided by the search program FOUNDATION (Ho & Marshall, 1993, supra). FOUNDATION uses a clique-detection algorithm (various algorithms are reviewed and compared in Brint & Willett, 1987, J. Mol. Graphics 5 49 and Brint & Willett, 1987, Chem. Inf. Comput. Sci. 27 152) which searches a 3D database of entries for a user-defined query consisting of the coordinates of various atoms and/or bonds of a 3D structural feature. FOUNDATION identifies all possible entries that contain any combination of a user-specified minimum number of matching atoms and/or bonds as hits.

Despite the usefulness of 3D database searching as a means of identifying structurally related proteins, this approach has not been well utilized with respect to engineering proteins with a desired function.

OBJECT OF THE INVENTION

The present inventors have recognized that 3D database searching is useful for identifying proteins which have one or more desired structural features, such proteins being candidate "frameworks" for the subsequent engineering of proteins with desired characteristics or functions. Furthermore, the present inventors have realized that protein engineering is best achieved by modification of a framework protein to incorporate particular amino acid residues required for a characteristic, property or function, rather than by incorporating entire elements of secondary structure such as loops or helices. This is particularly applicable when functionally important amino acids are scattered throughout a protein and are not confined to particular regions of primary or secondary structure.

It is therefore an object of the present invention to provide a novel method of protein engineering.

SUMMARY OF THE INVENTION

In one aspect, the present invention resides in a method of protein engineering including the steps of:—

(i) creating a computer database which includes a plurality of entries, each said entry corresponding to a description of a location and orientation in 3D space of side chains of amino acid residues of a framework protein, wherein the location and orientation of each side chain is simplified as a Cα–Cβ vector;

(ii) creating a query corresponding to a description of a location and orientation in 3D space of respective side chains of two or more amino acid residues of a sample protein which are required for a function of said sample protein, wherein the location and orientation of each side chain is simplified as a Cα–Cβ vector; and (iii) searching said database with said query to thereby identify one or more hits wherein at least one of said hits corresponds to a respective said framework protein which has structural similarity to said sample protein.

Preferably, the framework protein is capable of internal disulfide bond formation. More preferably, the framework protein is a small cysteine-rich protein comprising 70 amino acids or less, having 2–11 disulfide bonds.

In another aspect, the present invention provides a method of protein engineering including the steps of:—

(i) creating a computer database which includes a plurality of entries, each said entry corresponding to a description of a location and orientation in 3D space of amino acid residues of a framework protein capable of internal disulfide bond formation;

(ii) creating a query corresponding to a description of a location and orientation in 3D space of two or more amino acid residues of a sample protein which are required for a function of said sample protein; and (iii) searching said database with said query to thereby identify one or more hits wherein at least one of said hits corresponds to a respective said framework protein which has structural similarity to said sample protein.

Preferably, the framework protein is a small cysteine-rich protein comprising 70 amino acids or less, having 2–11 disulfide bonds.

Preferably, the location and orientation of each amino acid side-chain of said framework protein and said sample protein is represented by a Cα–Cβ vector.

In one embodiment applicable to the first- and/or second-mentioned aspects, the method includes the step of modifying an amino acid sequence of said framework protein which corresponds to a hit, by substituting at least one amino acid residue thereof with at least one amino acid residue of said sample protein.

Preferably, said at least one amino acid residue of said sample protein represents at least a portion of a functional region of said sample protein.

More preferably, at least two of the amino-acid residues of said sample protein which substitute amino acid residues of said framework protein are non-contiguous in primary sequence.

Preferably, the modified framework protein has greater stability than said sample protein.

Preferably, the framework protein so modified has increased structural similarity to said sample protein.

Advantageously, the modified framework protein is capable of exhibiting a function which is either similar to, or inhibitory of, a function of said sample protein.

In one embodiment, said sample protein is a cytokine selected from the group consisting of GH, IL-4, IL-6 and G-CSF.

In yet another aspect, the invention provides an engineered protein comprising 70 amino acid residues or less of a framework protein and 2–11 disulfide bonds of said framework protein, together with at least two amino acids of another protein which are non-contiguous in primary sequence and which represent at least a portion of a functional region of said another protein.

Preferably, the engineered protein has greater stability than said another protein.

More preferably, the engineered protein exhibits a function either similar to, or inhibitory of, said another protein.

In one embodiment, said another protein is a cytokine selected from the group consisting of GH, IL-4, IL-6 and G-CSF.

In a particular embodiment, the engineered protein has an amino acid sequence selected from the group consisting of the amino acid sequences of SCY01, SCY02, SCY03, ERP01, ERP02, ERP03 and VIBO1.

In still yet another aspect, the present invention resides in a computer program for searching a protein structure database.

In one embodiment, the computer program is for searching a protein database comprising a plurality of entries, each said entry corresponding to a distance matrix representation of two or more Cα–Cβ vectors, said program including the steps of:

(i) comparing a query with each said database entry, said query corresponding to a distance matrix representation of two or more Cα–Cβ vectors; and (ii) identifying hits by clique detection, wherein a hit is defined according to a minumum number of Cα–Cβ vector matches between said query and each said entry.

Throughout this specification and claims which follow, unless the context requires otherwise, "comprise", "comprises" and "comprising" are used inclusively, so that a stated integer or integer group does not exclude other integers or integer groups.

It will also be appreciated that throughout this specification and claims, scientific terms are to be given their usual scientific meaning, although certain terms are defined herein to assist interpretation by the skilled person.

BRIEF DESCRIPTION OF THE FIGURES AND TABLES

Table 1: An example of a query file which defines the query Cα–Cβ vectors, the tolerance for each query atom and the definition of a subset.

Table 2: Blood serum stability test results of a solution of SCY01.

Table 3: Enzyme stability test results of a solution of SCY01.

FIG. 1: Amino acid sequences of the hGH high affinity site antagonist framework scyllatoxin, the hGH antagonists SCY01, SCY02, SCY03 and their alignment with the hGH sequence. Disulfide linkages are indicated by lines connecting cysteines. Figure discloses SEQ ID NOS: 1–6, respectively, in order of appearance.

Figure 2:
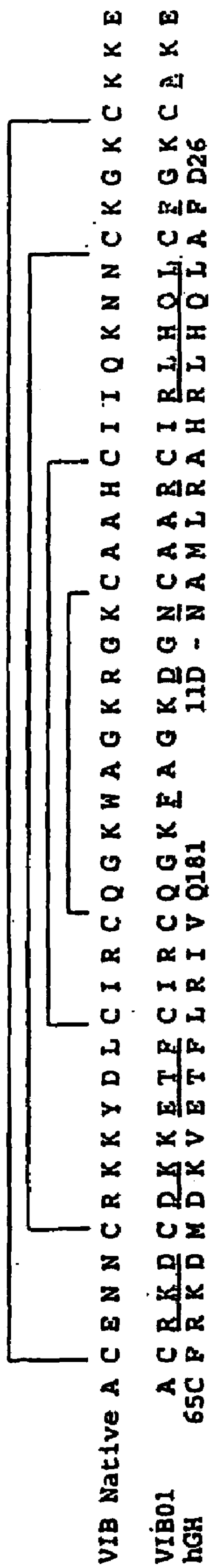

FIG. 2: Amino acid sequences for the hGH agonist framework VIB, the engineered molecule VIB01 and the alignment with the hGH sequence. Disulfide linkages are indicated by lines connecting cysteines. Figure discloses SEQ ID NOS: 7–10, respectively, in order of appearance.

Figure 3:
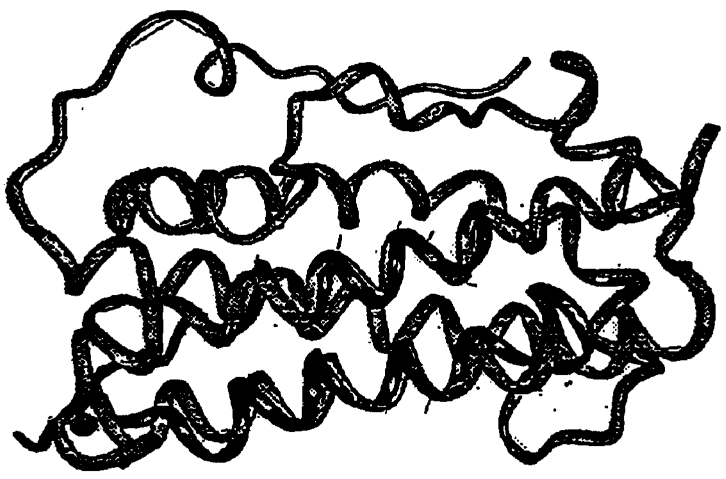

FIG. 3: Comparision of the hGH structure with hGH agonist molecule VIB01 showing the very high degree of overlap of the alpha helices.

Figure 4:
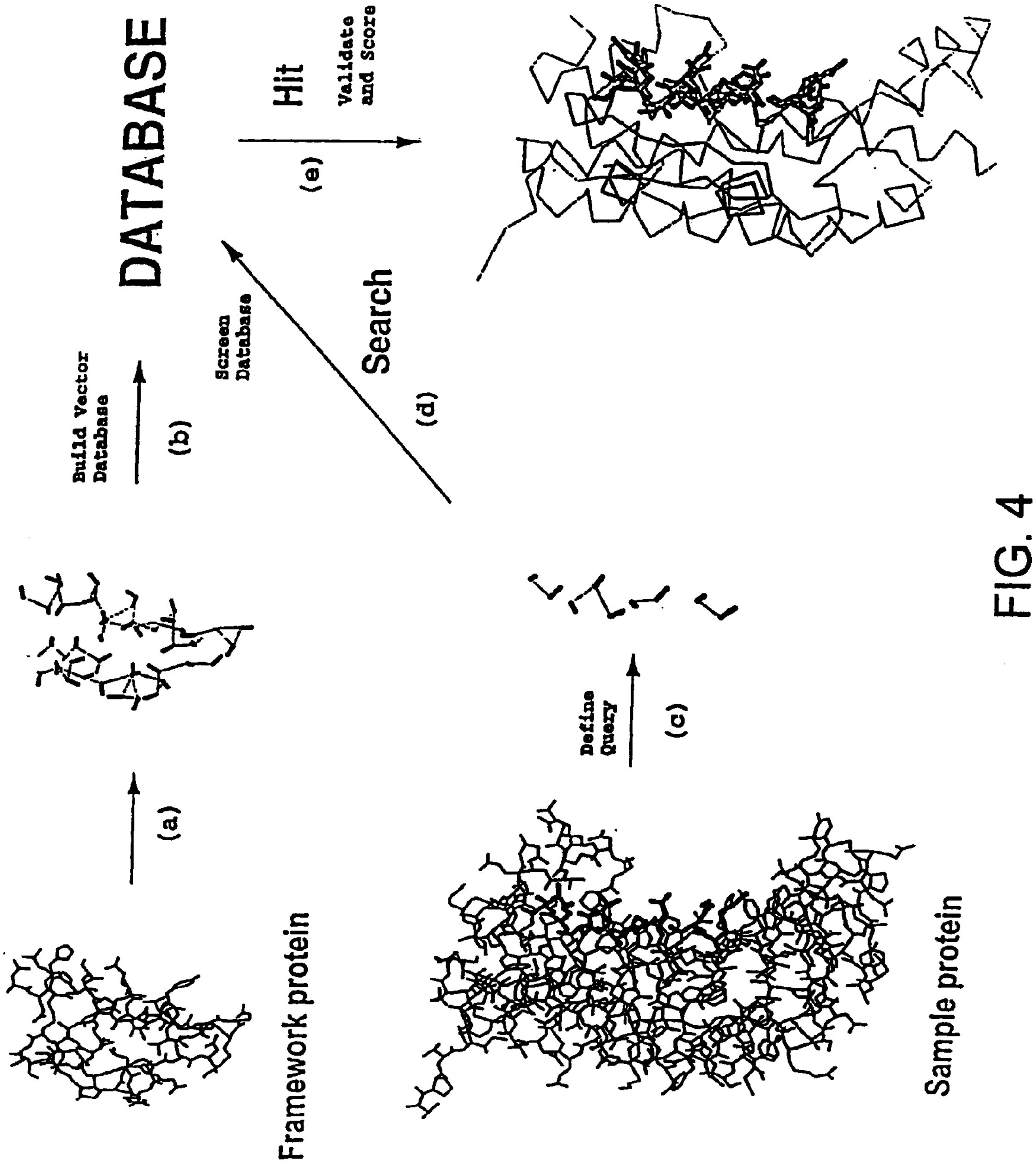

FIG. 4: Schematic overview of database searching strategy.

Figure 5:
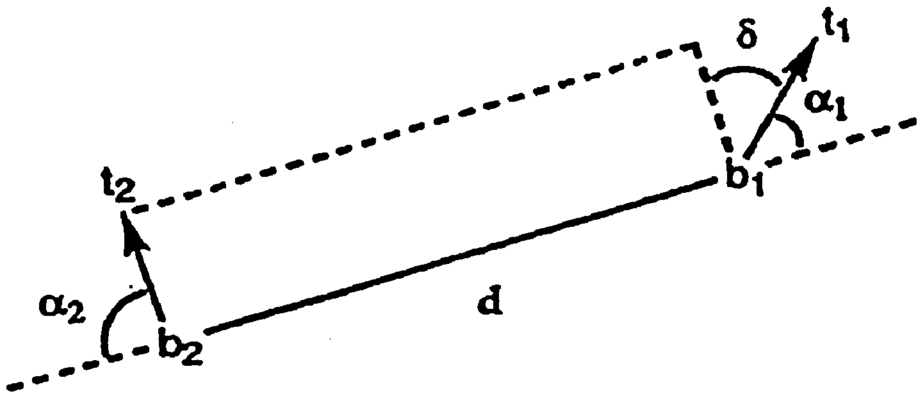

FIG. 5: Two-dimensional depiction of three different representations of a pair of Cα–Cβ vectors: d=interatomic distance as used to construct distance matrices; δ=dihedral angle; $\alpha_1$ and $\alpha_2$ angles.

Figure 6:
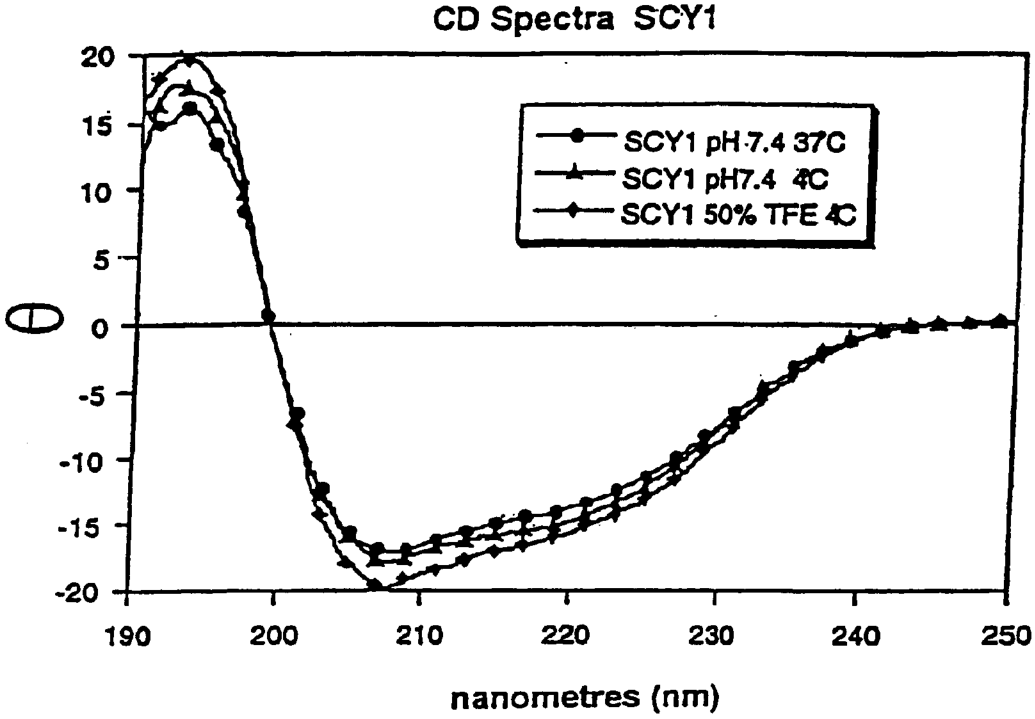

FIG. 6: Circular dichroism spectra of SCY01 showing little change in the structure on temperature changes or on the addition of helix stabilizing agent Trifluroethanol.

Figure 7:
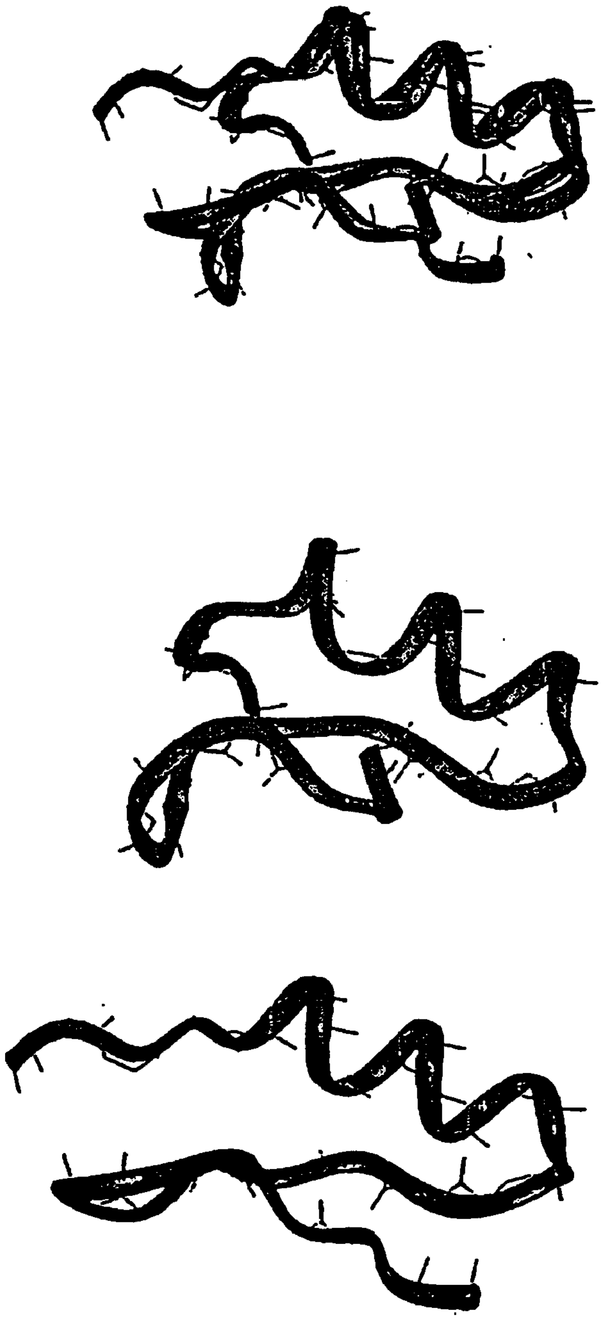

FIG. 7: Structure of the engineered SCY01 molecule shown in comparision with the native scyllatoxin molecule.

Figure 8:
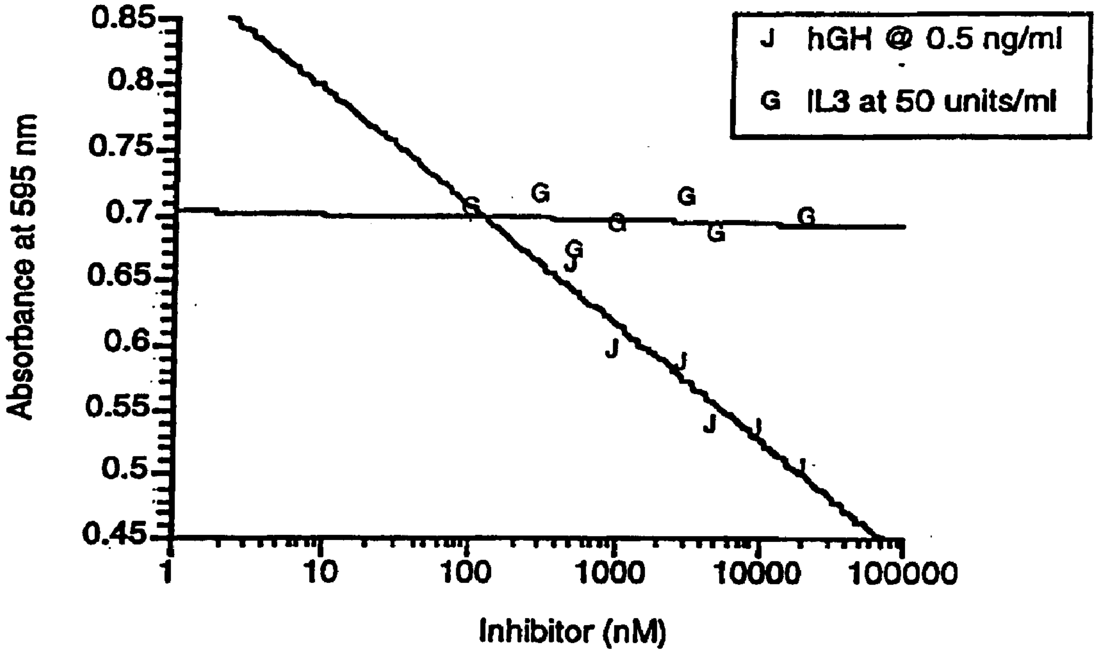

FIG. 8: Biological effect of SCY01 on BaF3 cell proliferation by inhibiting the growth response of the cells to 0.5 ng/mL hGH, but not to 50 U/mL IL-3.

FIG. 9: Amino acid sequence for the low affinity site hGH anatagonist framework ZDC and the engineered hGH anatagonist ZDC05 and the aligned hGH sequence. Disulfide linkages are indicated by lines connecting cysteines. Figure discloses SEQ ID NOS: 11–14, respectively, in order of appearance.

Figure 10:
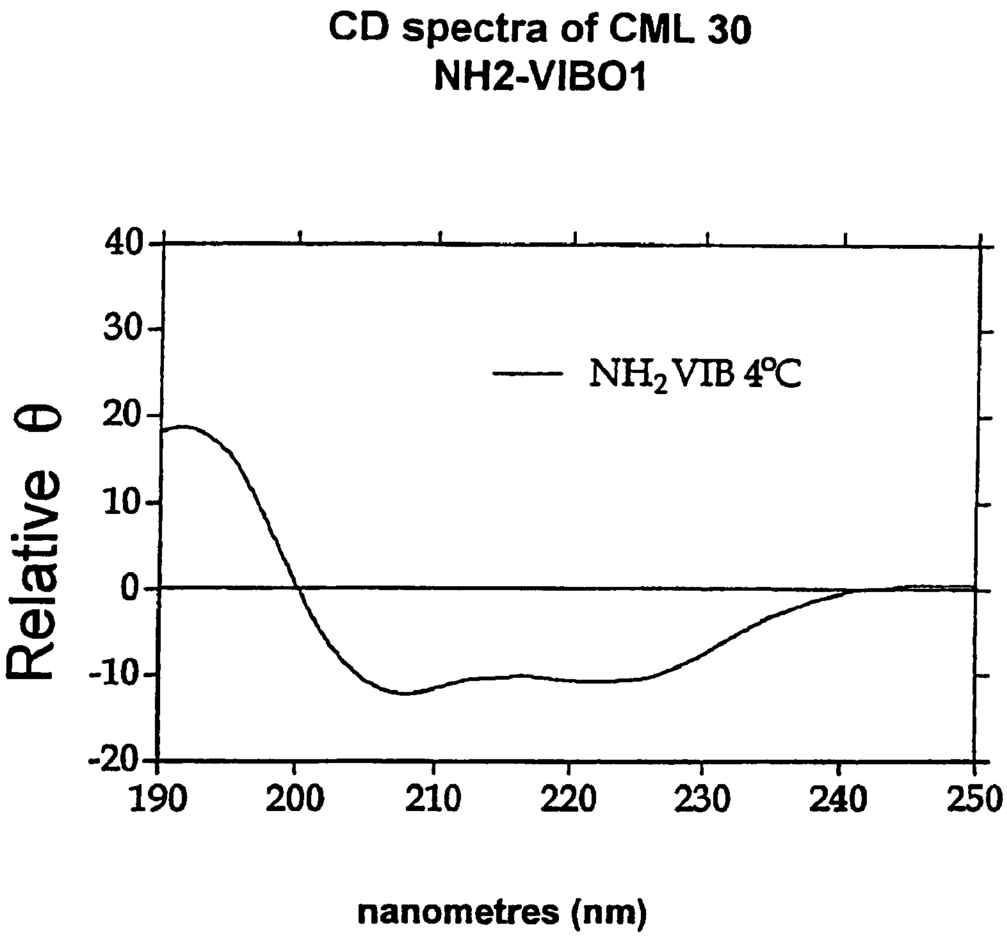

FIG. 10: Circular dichroism spectra of VIB01.

FIG. 11: Amino acid sequences of the hGH agonist framework ERP, the engineered molecules ERP01, ERP02, ERP03 and their alignment with the hGH sequence. Disulfide linkages are indicated by lines connecting cysteines. Figure discloses SEQ ID NOS: 15–20, respectively, in order of appearance.

Figure 12:
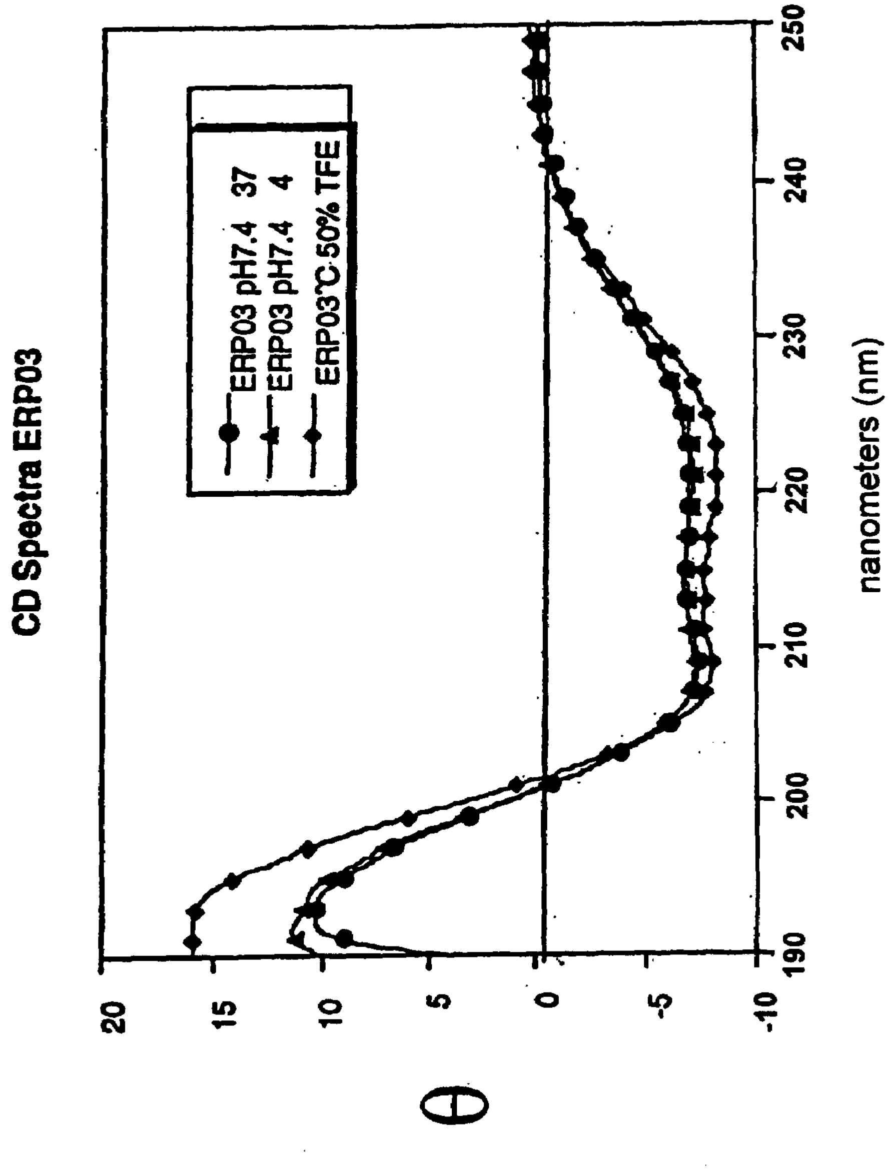

FIG. 12: Circular dichroism spectra of ERP03 showing little change in the structure on temperature changes or on the addition of helix stabilizing agent Trifluroethanol.

Figure 13:
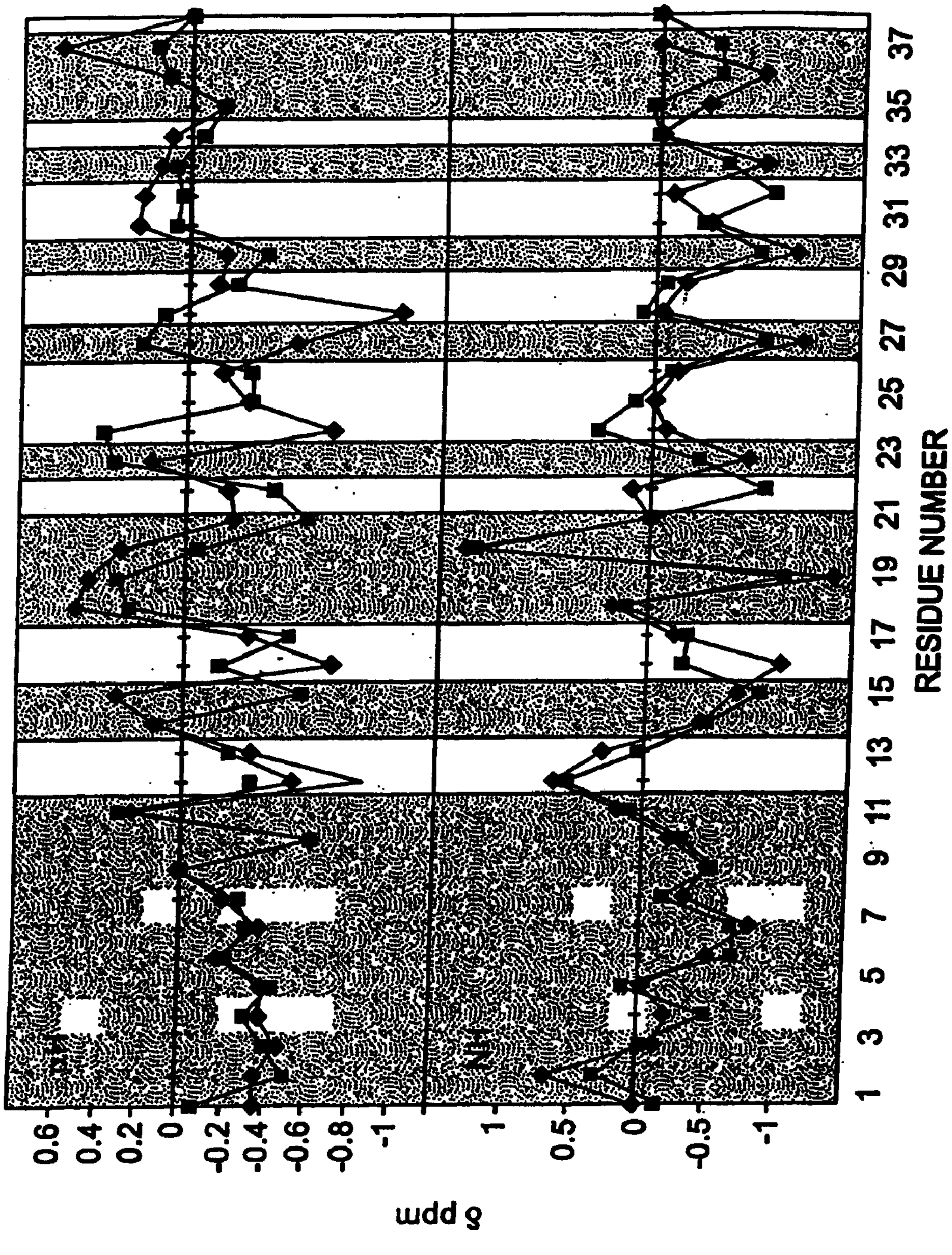

FIG. 13: Comparison of secondary Hα shifts for ERP01 and ERP03 showing substantially identical structure and disulphide connectivities. The shaded bars show the invarient residues of the native ERP molecule.-■-=ERP03 δHA; -◆-=ERP δHA.

Figure 14:
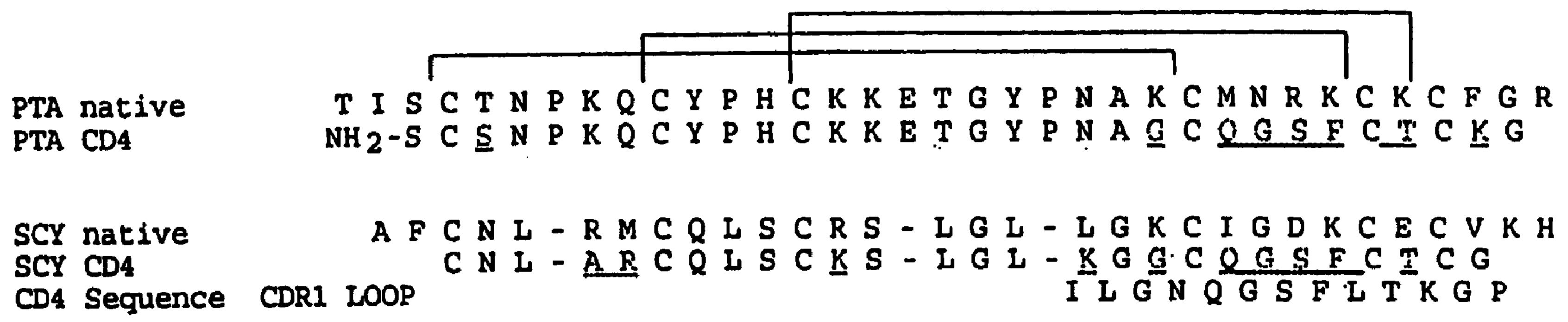

FIG. 14: Amino acid sequences of the CD4 frameworks PTA and SCY, the engineered molecules PTA CD4, and SCY CD4 and the alignment with the CD4 sequence. Disulfide linkages are indicated by lines connecting cysteines. Figure discloses SEQ ID NOS: 21–25, respectively, in order of appearance.

DETAILED DESCRIPTION OF THE PREFERRED EMBODIMENTS

It will be appreciated that the present invention is predicated, at least in part, on the present inventors' realization that in order to identify framework proteins suitable for further modification by protein engineering, it is advantageous to search databases according to the orientation in 3D space of constituent amino acid side-chains of the framework protein, with respect to constituent amino acid side-chains of the sample protein which is the subject of the query. Framework protein "hits" so identified suitably share similarity, such as in terms of topography and chemistry, to the sample protein "query" and as such may be suitable candidates for further modification. A particular aspect of the present invention is that a modified framework protein may display one or more desired characteristics, such as increased stability and in some cases a function similar to or inhibitory of the sample protein.

Referring to the method of the first- and second-mentioned aspects, preferably, each said entry corresponds to a description in the form of a distance matrix representation of said Cα–Cβ vectors.

Alternatively, said Cα–Cβ vectors may be represented by dihedral angles or $\alpha_1$ and $\alpha_2$ angles.

As used herein, "protein" and "polypeptide" are used interchangeably with regard to amino acid polymers. A "peptide" is a protein which has no more than fifty (50) amino acids.

As used herein, a "framework protein" is any protein which exhibits one or more desired structural features which provide advantages which include size, solubility and/or stability. "Stability" in this context includes resistance to degradation by proteolytic enzymes and/or temperature variation and/or resistance to denaturation by chaotropic agents and/or denaturing detergents, changes in pH, pH extremes, and/or REDOX extremes and/or changes.

The framework protein may be capable of internal disulfide bond formation. Preferably, said framework protein comprises 70 amino acids or less, having 2–11 disulfide bonds, which is an example of "a small cysteine-rich protein".

The amino acids used for creating each said entry may include some or all of the constituent of amino acids of the framework protein.

As used herein, a "sample protein" is a protein which has one or more functional characteristics of interest which render it desirable for the purposes of protein engineering.

Suitably, the sample protein may be an enzyme, nucleic acid-binding protein, cytokine, antigen, receptor, ion channel, chaperonin, or any protein with a function of interest.

In an embodiment, said sample protein is a cytokine selected from the group consisting of GH, IL-4, G-CSF, IL-6 and EPO.

Preferably, said function of said sample protein comprises binding a specific receptor to thereby elicit a biological response. However, a variety of other functions are contemplated, such as catalysis, binding cations ($Zn^{++}$, $Ca^{++}$, $Mg^{++}$), transporting ions (e.g. $Cl^-$, $K^+$, $Na^+$), binding lipids, binding nucleic acids as a means of transcriptional regulation or regulating DNA replication, assisting protein folding and transport, and any other function carried out by proteins.

With regard to creating a query, it is preferred that each said query corresponds to a description in the form of a distance matrix representation of Cα–Cβ vectors. However, other representations such as dihedral angles or $\alpha_1$ and $\alpha_2$ angles may also be applicable.

Preferably, said computer program used for searching said database is the VECTRIX program, as will be described in detail hereinafter. VECTRIX incorporates the FOUNDATION algorithm (Ho & Marshall, 1993, supra, which is herein incorporated by reference). Program FOUNDATION searches 3D databases of small organic molecules to identify structures that contain in any combination of a user-specified minimum number of matching elements of a user-defined query. It achieves this by first using a distance matrix to define the topography of the query atoms, followed by screening using various query constraints which define the chemical nature of the structure. The topology of the atoms in the structure are again represented using a distance matrix. Structural fragments in the database, whose distance description matches those of the query are identified using graph theory (Gibbons *Algorithmic Graph Theory*; Cambridge University Press: Cambridge, 1988).

In graph theory, a graph is a structure comprised of nodes (vertices) connected by edges. A graph is completely connected when all nodes are connected to one another. A subgraph is any subset of a larger graph. The largest completely connected subgraph of any graph is called a clique. Thus, the query is a completely connected graph, as all interatomic distances are determined in the distance matrix. The task is then to search a structural database to find all cliques that contain at least a user-defined number of matching nodes.

There are many clique-finding algorithms. Some of the well known procedures include those by Bonner, 1964, IBM J. Res. Develop., 8 22; Gerhards & Lindenberg, 1981, Computing 27 349 and Bron & Kerbosch, 1973, Commun. ACM 16 575. Computational chemists have adapted these algorithms or implemented similar ideas to facilitate searching for 3D structures within databases (Kuntz et al., 1982, J.

Mol. Biol. 161 269; DesJarlais et al., 1988, J. Med. Chem. 31 722; DesJarlais et al., 1990, Proc. Natl. Acad. Sci. 87 6644; Crandell & Smith, 1983, J. Chem. Infr. Comput. Sci. 23 186; Brint & Willett, 1987, J. Mol. Graphics 5 49–56; Kuhl et al., 1984, J. Comput. Chem. 5 24 and Smellie et al., 1991, J. Chem. Inf. Sci. 31 386).

Computer Database Searching

Vectrix

The present inventors have created a program "VECTRIX", which is a modified version of the clique-detection algorithm in program FOUNDATION as described by Ho & Marshall, 1993, J. Comp. Aided. Mol. Des. 7 3–22. The search procedure is illustrated in Scheme A. The major changes in comparison to Ho & Marshall, 1993, supra include:—

- the query and database structures are both proteins;
- the query elements are a distance matrix defining the topography of Cα–Cβ vectors, not individual atoms as in FOUNDATION;

similarly, the database structure is defined as a Cα–Cβ vector distance-matrix and not every atom as in FOUNDATION;

- in FOUNDATION, a pair of atoms in a query is considered to match with a pair of atoms in an entry in the database if the atom-type and the distance between them are matched; in VECTRIX, a pair of Cα–Cβ vectors in a query is considered to match with a pair of Cα–Cβ vectors in an entry in the database if the four distances ($C\alpha_1$–$C\alpha_2$; $C\alpha_1$–$C\beta_2$; $C\beta_1$–$C\alpha_2$; $C\beta_1$–$C\beta_2$) between the pairs are matched; and
- the FOUNDATION program performs the clique detection, steric filtering and subset filtering together and outputs the hits that satisfy the three criteria; by design, the VECTRIX program output all hits that have number of matches greater than or equal to MIN_MATCH. POSTVEC is then used to filter those hits based on steric filtering, a new MIN_MATCH and subset consideration; by separating the clique detection hits and the filtering process, the VECTRIX program is more flexible.

An outline of a program written by the present inventors is shown in Scheme A.

The VECTRIX program requires four parameters: (1) query.file (2) database.file; (3) steric.file and (4) MIN_MATCH. The parameters are described in detail below.

(1) query.file query.file (for example as in Table 1) contains the definition of the query, the definition of tolerance for each query atom and the definition of SUBSET. The three definitions are described below:—

Query definition: Prior to running the VECTRIX program, a particular target protein is selected. The target proteins three-dimensional structure must have been determined by experimental or theoretical means well known in the art. The functional amino acids of the target protein must be defined and the Cα–Cβ vectors for those functional residues extracted to the query.file. Table 1 shows the definition of Cα–Cβ vectors of four functional residues. The numbers in column 7, 8 and 9 represent the x, y and z coordinates of the vectors respectively.

Tolerance definition: The tolerance defines the allowable uncertainty in the orientation of each atom. Note that the final tolerance of a vector from atom A to atom B is the sum of the individual tolerance of atom A and B. In Table 1, the tolerances for individual atoms are defined in column 10 to be 0.5 Å, so the tolerance for a distance between two atoms is 1.0 Å.

Subset definition: A list of atoms can be grouped into a SUBSET. The query file allows for the definition of as many SUBSETs as are required. The SUBSET definition will be used in the POSTVEC program to filter the hits to obtain more relevant hits. In Table 1 the 1st SUBSET command is defined as subset 1 and it consists of Cα–Cβ vector numbers 1, 3 and 4. The 2nd SUBSET command is defined as subset 2 and it consists of Cα–Cβ vector number 2.

(2) database.file database.file contains a list of file names that correspond with the entries constituting the database.

(3) steric.file steric.file contains the coordinates of the grid points representing the ligand or receptor space. There are two forms of steric filtering depending on the availability of 3D structure of a receptor or ligand. If the structure of the receptor is known and a query is from the Cα–Cβ vectors corresponding to the receptor-binding amino acid side chains of a ligand, then a hit must be evaluated in terms of whether it would invade the 3D space accessed by the receptor upon binding a cytokine, for example (receptor-based filtering). Moreover, if the structure of the ligand is known and a query is from the Cα–Cβ vectors corresponding to the receptor-binding amino acid side chains of a ligand, then a hit must be evaluated in terms of whether it would invade the 3D space not occupied by the ligand (ligand-based filtering). The mode is identified in the first line of the 'steric file'. The first step in our steric filtering algorithm is the calculation of the grid points that represent the ligand or receptor 3D space using the program PREPARE_STERIC_FILTER. The program first defines the limits of the structure via determining the maxima and minima in the x, y and z dimension. Then for each grid points (1 Å apart) within the limit, a xyz coordinate is output to a 'steric file' if the point is in steric contact with the receptor or the ligand.

(4) MIN_MATCH

MIN_MATCH is an integer defining the minimum number of Cα–Cβ vectors that match between the query and the entry in the database required before VECTRIX will consider a clique as a hit.

Having entered the appropriate parameters, the first general step of the VECTRIX program is to calculate the distance matrix of the Cα–Cβ vectors of the query (see SCHEME A). Each database entry is now read in turn and the Cα–Cβ distance matrix of the framework protein is calculated. The clique detection algorithm of Ho & Marshall, 1993, supra, is used to identify geometric matches between the query and the database entry. If no match is found, another database file is read and processed. If a Hit is found, then some further processing is required because clique detection algorithm only finds the entries with Cα–Cβ vectors that match those in the query. It does not check for steric integrity, that is, the structural complementarity that each hit possesses with regard to the 3D space in which it must reside. The VECTRIX program uses the 'steric file' to calculate the number of atoms in the hit which invade the receptor space or the non-ligand space depending whether it is in receptor-based or ligand-based filtering mode. Some parts of the framework protein are not essential to binding to the target protein via the 'matched' functional residues. The non-essential part includes the side chains that are not in the matches, the N- or C-terminal residues, up to the matched residue or the first cysteine residue. The essential atoms of a residue are the backbone atoms (N, H, CA, HA, C, O) and the side chain atoms that are attached to the CA atom (CB, 1HA and 2HA). The essential residues are between the first and the last cysteine. If no cysteine is found in the protein, the essential residues are defined to be between the first and the last matched residues. The VECTRIX program counts and outputs the number of essential atoms as well as the number of essential atoms that invade the receptor or non-ligand space. Furthermore, for each subset of vector defined in the query file, the VECTRIX program counts and outputs the number of matched vectors in the subset. The results are written to an output file and another database entry is read and the process repeated until the end of the database is reached.

POSTVEC

By design, the VECTRIX program outputs all hits that have a number of matches greater than or equal to MIN_MATCH. The POSTVEC program is written for post VECTRIX filtering. The filtering is based on the steric contact, a new number of matches and the count of match in each SUBSET defined in the query.file. The POSTVEC program requires at least three parameters, i.e.

postvec vectrix_out.file min_match max_invade_fraction <subset1_num> <subset2_num> . . . <subsetX_num> where:

- the vectrix_out.file is the name of the vectrix output file.
- Min_match represents the new minimum number of matches required.
- the Max_invade_fraction defines the maximum allowable fraction of invasion of receptor/non_ligand space. That is, hits are rejected if the fraction of invasion is greater than the max_invade_frac. e.g. 0.1 for 10%.
- Subset1_num represent the number of matches required for subset1.
- Subset2_num represent the number of matches required for subset 2.
- the bracket < > denote optional parameters. That is, Subset parameters are optional, if they are not defined then there is no subset filtering.

The output of POSTVEC are pdbfiles of the filtered hits. These pdb files are in the same frame of reference as the query files, enabling simple display and comparison.

Examination of Hits Using Insight II

An Insight II macro, EXAMINE_HIT.BCL, was written to enable easy viewing of the hits obtained from POSTVEC. Before using EXAMINE_HIT.BCL, an InsightII .psv file, EXAMINE.PSV, must be created. This file contains the ligand or the receptor in the same reference coordinate as the query vectors. It is used as the background to display the hits. Normally the ligand/receptor are set to dull colours and the query vectors are highlighted with thick lines, Cα coloured red, and Cβ coloured yellow. In Insight II, sourcing the EXAMINE_HIT.BCL file will allow for visualisation of the hits through the next and previous button, or through clicking on the filename of the hit. The hits are displayed together with the query and the receptor/ligand. Steric contacts and matched vectors are highlighted.

An alternative representation of the VECTRIX program is shown in Scheme B.

Alternatively, other applicable clique detection algorithms are provided by Brint & Willett, 1987, J. Mol. Graphics, supra and Brint & Willett, 1987, Chem. Inf. Comput. Sci. supra, which are hereinafter incorporated by reference.

Using a series of automated scripts outlined in Scheme C, the database of small cysteine rich proteins is updated weekly by searching the Brookhaven database for suitable candidates.

Suitably, said one or more hits correspond to respective entries identified by said algorithm according to said query.

Should there be more than one hit, it is desirable to evaluate and rank each hit. The most important factor in evaluating hits is "steric integrity", or the 3D structural complementarity of a hit when compared to a query. Several algorithms have been developed which could be utilized for this purpose. Such algorithms would include an algorithm used by the FOUNDATION program, algorithms which check van der Waals overlap of each said hit with said query (Allinger et al., 1972, supra, which is herein incorporated by reference), or algorithms which calculate volume in common and volume of extra space with respect to each said hit and said query (Marshall et al., 1979, supra, which is herein incorporated by reference).

It is also contemplated that other algorithms may be useful. For example, simple distance calculations between said hit and said query after superimposition thereof may be used to identify 3D spatial differences therebetween.

An outline of the process that is currently used for scoring is given in Scheme D. These procedures post process output data from the POSTVEC program, and these procedures may eventually be incorporated into the program to provide a semi-automated process. In the current filtering process, steps 1 and 2 evaluate the conformational stability of the engineered hit, and step 3 provides optimization of the fit between a receptor and hit. Note that this filtering process is described with reference to scoring hits in terms of their predicted interaction with a receptor eg. a cytokine and cytokine receptor. One skilled in the art will realize that the principles outlined in Scheme D are applicable to any protein—protein interaction. For example, when a crystal structure is not known, scoring procedures can be implemented to ensure that the hit is subsumed by the steric surface of the ligand.

It is also envisaged that evaluation and ranking of each said hit may be achieved manually by a person skilled in the art, although this would be a less preferred method, particularly when there is a plurality of hits to be evaluated and ranked.

In light of the foregoing, the skilled person will understand that the method of the invention provides framework protein "hits" which may be the subject of further modification.

As used herein in this context, a framework protein hit has "structural similarity" to a sample protein by virtue of possessing amino acid sequence similarity, topographical similarity and/or chemical similarity. For example, a framework protein "hit" has a surface topography and/or chemistry which is similar to that of a receptor-binding region of a cytokine. Substitution of framework protein amino acids by sample protein amino acids preferably increases the degree of similarity.

Preferably, a framework protein identified as a hit has greater stability than the sample protein.

As used herein in this context, "stability" includes resistance to degradation by proteolytic enzymes and/or temperature variation and/or resistance to denaturation by chaotropic agents and/or denaturing detergents, changes in pH, pH extremes, and/or REDOX extremes and/or changes.

It will be appreciated that the said two or more amino acids used for creating a query at step (iii) of the method of the invention constitute at least a portion of one or more functional regions of said sample protein. These amino acids may be the same as, or different to, said at least one amino acid used in modifying the hit.

In one embodiment, an amino acid sequence of a framework protein which corresponds to a hit is modified by substituting at least one amino acid residue thereof with at least one amino acid residue of said sample protein. Preferably, the said at least one amino acid of the sample protein is/are selected from those required for a function of said sample protein. This engineering process can involve addition, deletion or insertion of amino acids as desired.

As already discussed, the purpose of such modification is to impart a particular property, characteristic or function to a framework protein. The method of the invention takes account of the fact that the amino acid residues essential to a particular function will often be non-contiguous with respect to primary sequence. These "scattered" amino acid residues may nevertheless form at least a portion of one or more functional regions, each of which occupies a distinct location and orientation in 3D space.

Advantageously, modification of the framework protein hit will be performed so as to effectively "transfer" one or more functional region(s) of the sample protein thereto. Transfer is achieved by incorporating amino acid residues from one or more functional regions (as hereinbefore defined) of the sample protein into an amino acid sequence of a framework protein. Such modification will be performed so as to engineer a protein which incorporates amino acid residues of said one or more functional region(s) appropriately located and oriented in 3D space.

In an embodiment, said framework protein is modified to function as a cytokine mimetic. In this regard, modification of a framework protein may be performed so that said framework protein is capable of exhibiting a function similar to that of said sample protein (such as in the case of an agonist), or alternatively, so that it inhibits a function of said sample protein (such as in the case of an antagonist).

However, the scope of the present invention extends to engineering proteins with any desired function by substituting amino acid residues of a framework protein. For example, an enzyme might be engineered to catalyze conversion of a substrate, or a transcription factor may be engineered to bind its cognate DNA sequence and to form complexes with other transcription factors necessary to promote transcription.

In the case where a cytyokine mimetic is to be engineered, a suitable approach is to modify an amino acid sequence of a framework protein (corresponding to a hit) by substituting amino acid residue(s) thereof with amino acid residue(s) of said cytokine selected from those amino acid residues which are required for binding of said cytokine to a specific receptor. Often, a biological response is elicited by a cytokine binding to two or more receptor molecules, thereby cross-linking said receptor molecules. A cytokine antagonist is therefore engineered by modifying a framework protein to include amino acid residues of a functional region required for binding one receptor molecule but not the other; an agonist is engineered by including amino acid residues of two functional regions, which together are required for binding and cross-linking of two receptor molecules. The functional regions required for binding said two receptor proteins occupy unique locations and orientations in 3D space. Engineering of an agonist therefore requires that the relative 3D location and orientation of each functional region is such that receptor binding and cross-linking is achievable.

In addition to direct substitution of amino acid residues of said cytokine selected from those amino acid residues which are required for binding of said cytokine to a specific receptor, several other design processes may be used. In cases where the atomic structure of the sample protein and its receptor are known, de novo design programs such as X-SITE (Laskowski et al., 1996, Journal of Molecular Biology, 175; Bohm, 1992, J. Comput. Aided. Mol. Des. 6 69, which are herein incorporated by reference) may be used to guide engineering of auxilliary binding epitopes into the hit that modulate activity. The auxilliary binding epitopes may be natural or unnatural amino acids that may be conjugated to additional functionality such as protecting groups used in synthetic peptide chemistry.

Programs that measure electrostatic similarity of mutated frameworks and the sample protein or electrostatic complementarity of the mutated framework and the sample protein receptor, such as DelPhi (Honig & Nicholls A, 1987, 'DelPhi', Computer Program, Department of Biochemistry and Molecular Biophysics Columbia University, which is herein incorporated by reference), may be employed to determine unmutated areas of the mutated framework that may be deleterious to activity.

Programs that measure buried surface areas, such as Naccess (Hubbard & Thornton, 1993, 'NACCESS', Computer Program, Department of Biochemistry and Molecular Biology, University College London, which is herein incorporated by reference) may be used to analyse and compare the buried surface areas of the sample protein and the mutated framework.

Often regions in proteins may be disordered and absent from the X-Ray or NMR structure. When residues are absent in the binding region of the sample protein, techniques such as homology modelling and loop searching may be employed to construct a complete model of the atomic coordinates.

Whichever approach is taken, modification of said amino acid sequence of said framework protein requires that considerations of maintaining stereochemical and secondary structural integrity apply. It is therefore important to be able to predict any structural effects induced in said framework protein by such modification. This can be accomplished with algorithms well known to the art as described in Bowie et al., 1991, Science 253 164–170; Luthy et al., 1992, Nature 356 83–85 and Laskowski et al., 1993, J. Appl. Cryst. 26 283–91.

Preferably, a modified framework protein would be chemically synthesized. Alternatively, this may be achieved by chemically synthesizing a polynucleotide sequence which encodes an amino acid sequence of said modified framework protein. Techniques applicable to the chemical synthesis of proteins and nucleic acids are well known in the art, and an example of such a technique will be provided hereinafter.

Alternatively, a polynucleotide sequence which encodes an amino acid sequence of a framework protein corresponding to said hit may be modified by in vitro mutagenesis techniques, resulting in a modified polynucleotide sequence encoding an amino acid sequence of said modified framework protein. Suitable in vitro mutagenesis techniques are well known in the art, such as described in Chapter 8 CURRENT PROTOCOLS IN MOLECULAR BIOLOGY (Ausubel et al., Eds; John Wiley & Sons Inc., 1995), which is herein incorporated by reference. Phage display is also contemplated, which technique is well known in the art. An exemplary phage display method is provided in Smith et al., 1998, J. Mol. Biol. 277 317, which is herein incorporated by reference.

According to one embodiment of the invention, each said entry in the database corresponds to a small cysteine-rich protein of not more than 70 amino acid residues, initially represented in Cartesian coordinate form, but subsequently processed into a distance matrix representation of Cα–Cβ vectors prior to searching. Said query is in the form of a distance matrix representation of Cα–Cβ vectors corresponding to amino acid side-chains of said sample protein, said amino acid side-chains being required for high-affinity binding of said sample protein to a receptor protein. In a particular embodiment, the sample protein is selected from group consisting of GH, IL-4, G-CSF and IL-6.

In the case where said sample protein is human Growth Hormone (hGH), and said receptor protein is human Growth Hormone Receptor (hGHR), the Cα–Cβ vectors of hGH are a simplification of the 3D location and orientation of the amino acid side-chains of hGH which contact hGHR during high-affinity binding, and are required for such binding.

In this case, said small cysteine-rich protein corresponding to a hit is scyllatoxin, the amino acid sequence of which (shown in FIG. 1) is modified so that a protein produced with that amino acid sequence is potentially capable of functioning as an hGH antagonist. The particular Cα–Cβ vectors used in the search process were Asp A171; Lys A172; Glu A174; Thr A175; Phe A176; Arg A178; Ile A179; Lys A41; Leu A45; Pro A48; Glu A56; Arg A64; and Gln A68. The particular amino acid residues of hGH incorporated into the amino acid sequence of scyllatoxin were selected from those required for high-affinity binding of hGH to hGHR (as shown above) and which topographically matched with residues of scyllatoxin. Determination of which amino acids of scyllatoxin could be substituted without drastically affecting structural integrity was achieved with the assistance of the INSIGHT II modelling program.

The SCY01–SCY03 peptides, designed as potential hGH antagonists, were chemically synthesised with the respective amino acid sequences shown in FIG. 1.

In another case, said small cysteine-rich protein corresponding to a hit is a marine worm toxin (VIB). Said hit was identified by database searching using a query which comprised Cα–Cβ vectors of the following hGH amino acid residues: Lys A41; Leu A45; Pro A48; Glu A56; Arg A64; Gin A68; Asp A171; Lys A172; Glu A174; Thr A175; Phe A 176; Arg A178; Ile A179; Arg A8; Leu A9; Asn A12; Leu A15; Arg A16; His A18; Arg A19; Tyr A103; Asp A116; Leu A117; Glu A119; and Thr A123.

An amino acid sequence of said hit (VIB) is shown in FIG. 2, and an amino acid sequence of proteins engineered by modifying one or more amino acids of said hit (VIB01) is shown in FIG. 2. The particular amino acid residues of hGH used to modify said hit were selected from those forming the agonist-binding functional region of hGH as indicated in FIG. 2. Overlap between hGH and said marine worm toxin is shown in FIG. 3, which serves to emphasize the ability of the method of the invention to identify hits which match cytokine agonist functional regions.

The peptides designed according to the hGH agonist regions consitute candidate hGH agonists.

In light of the foregoing, it will be understood that the present invention contemplates engineered proteins such as according to the second-mentioned aspect.

In one embodiment, the amino acids of said another protein present in the engineered protein represent at least one functional region of said another protein.

In another embodiment, the amino acids of said another protein present in the engineered protein represent two functional regions of said another protein.

As well as providing amino acids which are non-contiguous in primary sequence, said another protein may also provide amino acids which are contiguous in primary sequence.

In one embodiment, the engineered protein has an amino acid sequence selected from the group consisting of SCY01, SCY02, SCY03, ERP01, ERP02, ERP03 and VIBO1.

It will also be appreciated that according to both the first and second aspects of the invention, homologs of engineered proteins are contemplated. A person skilled in the art will realize that conservative amino acid substitutions, deletions and additions can be made such that a protein will retain a particular function notwithstanding such changes in amino acid sequence. All such homologs fall within the scope of the invention described herein.

In order that the present invention may be understood in more detail, the skilled person is directed to the following non-limiting examples.

EXAMPLES

Example 1

Overview of Database Search Strategy

A schematic description of the computational approach developed by the present inventors, program VECTRIX, is shown in FIG. 4. The first step involves the creation of a library of small cysteine-rich proteins. Currently, 344 such proteins (each with less than 70 amino acid residues) comprising over 3779 experimentally-derived 3D structures have been extracted from the BROOKHAVEN database. However, it would also be feasible to construct databases using theoretically derived features, such as by homology modelling, threading or other techniques known in the field.

Each structure is simplified, in turn, into Cα–Cβ vectors (step a), essentially resulting in a database of entries (step b). For the purposes of searching the database, each query is in the form of a distance matrix representation of Cα–Cβ vectors (step c). However, it is possible to represent Cα–Cβ vectors by other means, such as dihedral angles (δ) or $\alpha_1$ and $\alpha_2$ angles. A simple description of these types of representations with respect to a Cα–Cβ vector pair is shown in FIG. 5.

The search algorithm compares the distance matrix representing the query Cα–Cβ vectors with the distance matrix representing Cα–Cβ vectors of each entry (step d). Comparison of topographical similarities was chosen because Cα–Cβ vectors are common to all amino acid side chains (except glycine), and are essentially anchored to the backbone. They therefore represent the initial orientation of the amino acid side chain in 3D space, which would probably not undergo significant change upon interaction with another protein. It is envisaged that the extra atoms of the side chain will provide some degree of induced fit during such an interaction.

Alternative, more restricted approaches would use secondary structural features such as α-carbon backbone structures, together with suitable algorithms well known in the field (Holm & Sander, 1994, supra; Alexandrov, 1996, supra; Alexandrov & Fisher, 1996, supra; and Oreng, 1994, supra).

The intermolecular geometric relationship of Cα–Cβ vectors is compared using the clique-detection algorithm of Ho & Marshall, 1993, supra, which identifies hits according to a user-defined number of minimum vector components. However, other algorithms well known in the art would also be useful in this regard.

As a result of step d, one or more hits may be identified. If a single hit is obtained, no ranking is necessary. If the number of hits is small, it may be possible for the skilled person to evaluate and rank each hit individually (step e). If, however, the number of hits is large, such manual comparison would be more difficult, and an automated process is required.

The most important factor in evaluating and ranking hits is steric integrity, that is, the structural complementarity that each hit possesses with regard to the 3D space in which it must reside. For example, if the query is in the form of a distance matrix representation of Cα–Cβ vectors corresponding to the receptor-binding amino acid side-chains of a hormone, then a hit must be evaluated in terms of whether it would invade the 3D space accessed by the receptor upon binding the cytokine. Several algorithms have been developed that are useful for this purpose. For example, the FOUNDATION program of Ho & Marshall, 1993, supra uses various flood filling algorithms to define the 3D space occupied by the receptor (as determined from the crystal structure of the receptor), and then uses atom-checking routines to establish whether the atoms of a hit reside in the binding "cavity" of the receptor. Other approaches include placing molecules in a cube containing lattice points and checking the van der Waals overlap of each molecule (Allinger, 1972, In: Pharmacology and the future of Man. Proceedings of the 5th International Conference on Pharmacology pp 57–63). A related method involves the calculation of the volume in common and the volume of extra space of two molecules (Marshall et al., 1979, The Conformational Parameter in Drug Design: The active analog approach. 112 205).

It is also possible to use simple distance calculations between query and hit, after the two have been superimposed, to identify if the hit protrudes from the space occupied by the query structure. This is an approach the present inventors have implemented in an algorithm currently being constructed.

It is also important to be able to predict any drastic structural effects that may result from amino acid sequence changes when modifying a hit. This will, in part, be achieved by maximizing the degree of amino acid sequence identity of the modified hit with that of the protein (or area of the protein) to which the query corresponded. In addition, the stereochemical and degree of secondary structure disruption of the modified hit can be evaluated using standard algorithms which check protein stereochemistry on an amino acid by amino acid basis. Similarly, secondary structure prediction algorithms can be used to evaluate the potential for an amino acid sequence modification of a hit to disrupt secondary structure.

Finally, the present inventors plan to utilize molecular surfaces to compare various physicochemical properties of a query and hit. Charge, electrostatic potential, hydrophobicity, occupancy, and hydrogen bonding potential have all been mapped to protein surfaces, providing detailed comparisons between proteins. A method for quantitating the degree of similarity between two molecular surfaces has been developed, in which a gnomonic projection casts the calculated values of a given property onto a spherical surface (Dasnzinger & Dean, 1985, J. Theor. Biol. 116 215). Two such surfaces can then be superimposed using pairs of corresponding atoms. This algorithm would be very useful for comparing query protein with a hit, to allow fine tuning of amino acid residues of the protein corresponding to the hit, and to improve steric and electrochemical complementarity.

Since the database searching algorithms (such as provided by the VECTRIX program) applicable to the method of the invention allow for the identification of partial hits, there is scope for a skilled person to use molecular modelling to identify additional regions on the surface of the protein corresponding to the partial hit for mimicking vectors missed in the database search. This could involve the use of D-amino acids or non-coded amino acids, for example, to achieve better mimicry when engineering a mimetic.

In the following examples, the VECTRIX program has been applied to various sample proteins.

Example 2

High Affinity hGH Antagonists

Growth hormone (GH) is a pituitary cytokine that regulates many growth processes, such as the growth and differentiation of muscle, bone and cartilage cells. The growth cytokine receptor (GHR) consists of three domains:—

(i) an extracellular domain that binds GH;
(ii) a transmembrane domain; and
(iii) a cytoplasmic domain involved in eliciting an intracellular signal upon cytokine binding.

Intracellular signalling occurs as a result of dimerization of separate GHRs following sequential binding of each receptor to a single GH ligand. The first GHR binds to the high affinity site of GH, while the second GHR subsequently binds to this complex. In support of this model, the crystal structure of this complex shows two identical receptor molecules bound to dissimilar sites on a single human GH molecule (hGH; De Vos et al, 1992, Science 255 306).

The high affinity site on hGH is concave and buries approximately 1200 $Å^2$ of surface area, while the second binding site on hGH buries approximately 900 $Å^2$ of surface area. A third region contributing to the stability of the complex comprises an area of 500 $Å^2$ buried by the receptor—receptor interaction.

The crystal structure also reveals that the actual contact areas of both the high affinity and low affinity sites of hGH are buried upon complexation with the receptors.

In developing antagonists of hGH, the present inventors have sought to design molecules that mimic the high-affinity binding of hGH. Mutagenic studies of the amino acid residues within the high affinity binding site showed a dramatic decrease in affinity when certain of these amino acid residues were converted to alanine (Cunningham & Wells, 1993, 234 554). In this regard, of the 31 amino acid residues with buried side-chains, a mere eight (Lys A41; Lys A45; Pro A61; Arg A64; Lys A172; Thr A175; Phe A176; and Arg A178) accounted for approximately 85% of the total change in binding energy resulting from substitution by alanine. A further five residues (Pro A48; Glu A56; Gln A68; Asp A171; and Ile A179) essentially accounted for the remainder of the binding energy.

The GH residues currently used in the design of antagonists are: Asp A171; Lys A172; Glu A174; Thr A175; Phe A176; Arg A178; Ile A179; Lys A41; Leu A45; Pro A48; Glu A56; Arg A64; and Gln A68. It is these amino acid residues of hGH which formed the basis of the query for the purposes of database searching.

Scyllatoxin (pdb1scy) was returned as a hit framework that matched a maximum of 7 vectors of the hGH high affinity surface. After identification of a hit molecule, molecular modelling studies were used to optimise the hit resulting in the design of SCY01, SCY02 and SCY03.

For example, molecular modelling studies (using INSIGHT II) suggested that the C-terminal His of the scyllatoxin-based mimetics could be removed as it does not interact with the receptor. This has advantages when synthesising the target molecule as His have a potential to racemise during peptide assembly. As shown in FIG. 1, the mutated framework SCY01 was produced by transfer of 7 matching hGH residues, R167, K168, D171, K172, E174, T175 and F176. Similarly SCY02 was designed by transfer of hGH residues D171, K172, E174, T175, F176, R178 and I179, however the affinity matured hGH mutation E174S was incorporated into SCY02. Similarly, SCY03 incorporated the affinity matured hGH mutations D171S and E174S. In this fashion, several analogues were designed based on a single hit, that incorporated different functional residues and affinity matured residues.

In addition, molecular modelling techniques were used to optimise the amino acid functionality that was transferred to the new framework. Using the atomic structure of hGHR, X-SITE (Laskowski et al., 1996, supra) was used to predict binding sites for functional groups that could be incorporated into the hit peptide. Thus SCY13 was developed from SCY02 and SCY03 with the aid of the program X-SITE (Laskowski et al., 1996, supra), to incorporate novel mutations and auxilliary groups. As shown in FIG. 1, SCY13 possesses a D171Y mutation, a T175D mutation and an F176E(Fm) mutation. In addition, an N4R mutation in the native scyllatoxin sequence was also incorporated based on the X-SITE (Laskowski et al., 1996, supra) results. These mutations were incorporated to optimise the electrostatic interactions and to increase the bound surface area of the modelled SCY-hGHR complex.

Molecular modelling studies indicated that SCY01, SCY02 and SCY03 would bury approximately 700 Å$^2$ when bound to hGHR, whilst SCY13 would bury approximately 1000 Å$^2$ when bound to hGHR. The modelling program DelPhi (Honig, B. & Nicholls, A. (1987), 'DelPhi', Computer Program, Department of Biochemistry and Molecular Biophysics Columbia University) was used to compare the electrostatic potential maps of hGH and SCY peptides, with the conclusion that there was good complementarity between hGH and SCY peptides.

The scyllatoxin peptides SCY01–SCY03 and SCY13 (FIG. 1) were then synthesised using solid phase techniques (M. Schnolzer et al., 1992, International Journal of Peptide and Protein Research, 40 180–193) purified and oxidised. The products were fully characterised using mass spectrometry, high performance liquid chromatography (HPLC) and amino acid analysis (AAA). The secondary structure elements of the engineered SCY molecules were determined by circular dichroism on SCY01 and SCY02 (FIG. 6). The spectra showed a high helical content consistent with the native SCY fold. In addition, CD indicated that the helical structure was unchanged by addition of helical stabilizing agents such as TFE or destabilizing agents such as Guanidine.HCl or temperature. This emphasises the favourable chemical characteristics of these frameworks.

In order to determine that the new engineered SCY framework mimics the structure of the region of GH used as a query, the structure of SCY01 was determined by NMR spectroscopy. As illustrated in FIG. 7, we found that their is close conformational overlap (RMS 0.45 Å) between the functional residues on GH and the engineered surface of SCY01. Thus validating the process of selecting a target protein, simplifying the functional epitope into Cα–Cβ vectors, using these as a query to identify new frameworks that match the shape of this query, synthesising, characterising and folding the new engineered framework. The resulting new engineered framework structurally matches that of the functional epitope of the target protein, thus validating the design process.

In order to characterise the folding patterns of SCY02 and SCY03 NMR experiments were again carried out. However, this time the secondary shifts were compared (Wishart et al., J. Biomolecular NMR 5 67) between the engineered and native SCY. As expected there is little or no deviation in the CHα or NHα shifts compared to the native SCY molecule indicating the correct fold and disulphide bond connectivity.

SCY01 was tested for biological function by bioassay using the BaF3 cell line, which cells normally respond to GH. The results are shown in FIG. 8. SCY01 was assayed at various concentrations to check its ability to inhibit BaF3 cell proliferation in response to either 0.5 ng/mL hGH, or as a control, 50 Units/mL IL-3. The calculated $K_i$ from these experiments was approximately 200 μM, and no inhibitory activity was observed with respect to IL-3 induced proliferation. Thus, SCY01 displayed an inhibitory activity with respect to GH-stimulated proliferation. This biological effect suggests that SCY01 is a candidate for further investigation with regard to it's mechanism of action.

The SCY peptides showed extremely good stability in the hGH assay buffer as judged by HPLC of the peptide at various time points after incubation in the assay buffer for up to 72 hrs. Preliminary studies evaluated the bioavailability of SCY01 by exposing it to a variety of proteases (trypsin, chymotrypsin and pepsin) and blood serum proteins as described in MATERIALS AND METHODS. The results of the blood serum stability test are presented in Table 2, and the results of the enzyme stability tests are presented in Table 3. The SCY peptide was found to be stable after 24 hrs in each case, while control peptides were rapidly digested. Thus emphasising the favourable chemical characteristics of disulfide-rich proteins.

In this example the present inventors have taken a functional epitope of hGH and successfully engineered it onto a new disulfide-rich framework. This framework has appealing chemical characteristics in terms of bioavailability and bioactivity when compared to macromolecular proteins.

Experimental to Example 2

Vectrix Results

Number of vectors searched: 15—R167, K168, D171, K172, E174, T175, F176, R178, I179, K45, P48, E56, R64, Q68.

Number of Different Frameworks Selected (Name:pdb code Number Vector Matches):

Scyllatoxin: pdb1scy (7)

Synthesis

As described in the General Materials and Methods section. The peptides were fully characterized by mass spectrometry, Reverse Phase High Performance Liquid chromatography (RP-HPLC) and Amino acid analysis (AAA).

Folding

The pure reduced peptides SCY 01–03 were folded using 0.1 M solution of $NH_4HCO_3$ stirred overnight at RT at a peptide concentration of ~0.3 μM per ml monitored by HPLC and mass spectrometry. The folded peptide was isolated by preparative HPLC and mass spectrometry. The folded peptide was isolated by preparative HPLC. The correct disulphide connectivity for SCY01 was determined by full structure analysis by NMR. Folding methods using oxidized and reduced glutathione in a ratio of 100:10:1 GSH:GSSG:peptide (GSSG disclosed as SEQ ID NO: 26) and published methods using 5 mM GSSG (SEQ ID NO: 26) to 0.5 mM GSH in $NaPO_4$ buffer pH 7.4 was carried out it give identically folded material. After folding the pure peptide an equivalent yield of peptide was obtained by folding the crude peptide in exactly the same manner. The oxidation of SCY13 was complicated by the Fm group attached to the Glu. SCY13 was oxidised using a 30% TFE solution in the presence of 5 mM GSSG (SEQ ID NO: 26) to 0.5 mM GSH in $NAPO_4$ buffer pH 7.4.

Circular Dichroism (CD)

CD was performed as outlined in the General Materials and Methods section.

NMR

The NMR structure of SCY01 and the CHα and NHα connectivities were determined as outlined in the General Materials and Methods section.

Peptide Stability Tests

Stability in Assay Buffer

The SCY peptides showed extremely good stability in the hGH assay buffer (RPMI-1640 medium supplemented with 10% (v/v) foetal bovine serum (FBS) and 100 units/mL IL3. The peptides were incubated at 1 mg/ml solutions in the buffer at 37° C. Samples were removed at various time points and HPLC analysis showed the rate of peptide decomposition up to 72 hrs.

Blood Serum

Blood was collected in heparinised tubes by venapuncture. The blood was centrifuged at 5000 rpm for 20 mins and the serum decanted. The blood serum was stored at −20° C. A sample of the blood serum (900 μL) was incubated with 100 μL of the stock peptide solution (1 mg/mL in $H_2O$) at 37° C. and aliquots (100 μL) removed at the required time. A solution of 50% $CH_3CN$ 0.1% TFA was added to precipitate the blood serum proteins and centrifuged at 13000 rpm for 5 mins. A sample of this solution (100 μL) was analysed by RP-HPLC (Vydac C18 218TP54 250×4.1 mm id 1%/min gradient $H_2O/CH_3CN$ 0.1% TFA) to detect peptide digestion.

Enzyme Stability Test.

Trypsin

To the peptide solution ($NH_4HCO_3$, pH 8.3, 0.87 mg/mL) was added trypsin (5% w:v). Samples were incubated at 37° C. and aliquots removed at 0, 1, 3 and 18 hrs and analysed by RP-HPLC as above.

Chymotrypsin

To the stock peptide solution (100 μL) was added 900 μL $NH_4HCO_3$ (pH 8.3). Chymotrypsin was added to 5% w:v and incubated at 37° C. Aliquots were removed at 0 hr, 1 hr and 24 hrs and analysed by RP HPLC.

Pepsin

To the stock peptide solution (100 μL) was added $H_2O$ (800 μL) and 0.1 M HCl (100 μL) to pH 2.2. Pepsin was added to give a 1% w:v solution and incubated at 37° C. Aliquots were removed at 0 h, 1 h and 24 hrs and analysed by RP-HPLC.

Example 3

Growth Hormone-Low Affinity Site

The low affinity site of growth hormone comprises at least 12 residues. The Cα–Cβ vectors of these 12 residues were used in a VECTRIX search. Pdb1zdc (ZDC) was returned as the best hit with 9 search vectors matched at 1 Å tolerance. These residues were R8, L9, D11, N12, L15, R16, R19, D116 and E119. Molecular modelling (Insight II) was again used to optimise the hit. It was decided that the R29L (matching L9 of hGH) may disrupt the ZDC fold and this mutation was not incorporated. Furthermore, additional molecular modelling studies suggested that ZDC could match a further 7 residues of hGH. The residues that matched (15 residues—RMSd backbone atoms between hit and hGH—1.46 angstroms) and were incorporated into ZDC05 were, R8, D11, N12, L15, R16, R19, Y111, D112, K115, D116, E118, E119, G120, Q122 and T123. As shown in FIG. 9, the mutated framework ZDC05 was produced by transfer of the above 15 matching hGH residues.

Experimental to Example 3

Vectrix Results.

Number of vectors searched: 12—R8, L9, D11, N12, L15, R16, R19, D112, L113, D116, E119, T123.

Number of different matches at 7 or more vector matches: 22

Number of unique frameworks at 7 or more vector matches: 6

Number of Different Frameworks Selected (Name:pdb Code Number Vector Matches):

Protein A engineered fragment: pdb1zdc (9)

Example 4

Growth Hormone Agonist I

The agonist site of hGH comprises 25 residues. The Cα–Cβ vectors of these 25 residues were used in a VECTRIX search. Pdb1vib (VIB) was returned as the best hit with 8 search vectors matched. These residues were N12, R16, R19, D171, K172, E174, T175 and F176. Molecular modelling determined that VIB could match a further 9 residues of hGH. The residues that matched (17 residues—RMSd backbone atoms between hit and hGH—0.86 angstroms) and incorporated into VIB01 were D11, N12, R16, R19, L20H21, Q22, L23, F25, R167, K168, D169, D171, K172, E174, T175 and F176. As shown in FIG. 2, the mutated framework VIB01 was produced by transfer of the above 17 matching hGH residues.

The modelling program Delphi (Honig & Nicholls, 1987, supra) was used to compare the electrostatic potential maps of hGH and the mimics, with the conclusion that there was good complimentarity between hGH and the mimics.

With the aid of molecular mechanics forcefield minimisations and molecular dynamics, VIB01 was determined to position the mutated residues in appropriate spatial orientations to mimic hGH and to retain the native fold.

The VIB peptide (FIG. 2) was synthesised using solid phase techniques (M. Schnolzer et al., International Journal of Peptide and Protein Research, supra), purified and oxidised. The product was fully characterised using mass spectrometry HPLC and AAA. The secondary structure elements of the engineered VIB molecules was checked by circular dichroism as illustrated in FIG. 10. The engineered VIB peptide had a very stable structure and shows significant helical character in aqueous conditions. This would be expected as the native fold is a helix loop helix motif.

In addition, the VECTRIX search identified peptide ERP as a hit with 7 search vectors matched. These residues were N12, L15, R16, H18, R19, T175 and R178. Molecular modelling determined that ERP could match a further 6 residues of hGH. The residues that matched (13 residues—RMSd backbone atoms between hit and hGH—1.33 angstroms) and were incorporated into ERP01 were R8, D11, N12, M14, L15, R16, H18, R19, E174, T175, F176, R178 and I179. As shown in FIG. 11, the mutated framework ERP01 was produced by transfer of the above 13 matching hGH residues.

The modelling program DelPhi (Honig & Nicholls, 1987, supra) was used to compare the electrostatic potential maps of hGH and the mimics, with the conclusion that there was good complimentarity between hGH and the mimics.

With the aid of molecular mechanics forcefield minimisations and molecular dynamics, ERP01 was determined to position the mutated residues in appropriate spatial orientations to mimic hGH and to retain the native fold.

ERP02 differed from ERP01 in containing the hGH affinity matured mutations E174S, I179T and H18D. The G14F mutation (F176 mimic) in ERP01 and ERP02 necessitated two major mutations, S6G and N11G. ERP03 eliminated the G14F mutation and the necessity for these mutations giving a less perturbed sequence.

The ERP peptides 01–03 (FIG. 11) were synthesised using solid phase techniques (M. Schnolzer et al., International Journal of Peptide and Protein Research, supra), purified and oxidised. The product was fully characterised using mass spectrometry HPLC and AAA. The secondary structure elements of the engineered ERP molecules was checked by circular dichroism on ERP03 (FIG. 12). This showed a very high degree of alpha helical character in agreement with the 3 helical bundle structure of the native ERP molecule.

NMR of ERP01 and ERP03 was carried out to check that the 3 disulfide bonds have formed correctly. As expected there is only small deviation from the native ERP molecule where the mutations to mimic the hGH molecule are made (FIG. 13 for ERP03). There is little or no deviation in the CHα or in the NHα shifts compared to the native ERP molecule indicative of the correct folding and disulphide bond connectivity, once again emphasing the ability to engineer new surfaces onto disulfide rich peptides, whilst maintaining the native fold.

Experimental to Example 4: VIB

Vectrix Results

Number of vectors searched:25—R8, L9, N12, L15, R16, H18, R19, K41, L45, P45, E56, R64, Q68, Y103, D116, L117, E119, T123, D171, K172, E174, T175, F176, R178 and I179.

Number of Different Matches
61292 at minimum 5 vector matches

Number of Unique Frameworks
10 at minimum 7 vectors, 1 at minimum 8 vectors

Number of Different Frameworks Selected (Name:pdb Code: # Vector Matches)
Marine worm neurotoxin: pdb1vib (8)

Peptide Synthesis

Synthesis of the VIB peptides was as described in the General Materials and Methods section.

Oxidation of the VIB Peptides

The reduced VIB peptides were oxidsied using the methods outlined for the ERP peptides with 30% TFE solutions and GSSG: GSH oxidation shuttle.

Circular Dichroism

CD was performed as outlined in the General Materials and Methods section.

Experimental to Example 4: ERP Molecule

Synthesis of ERP Peptides

As described in the General Materials and Methods section.

Folding of ERP Peptides

The peptide was dissolved at a low concentration in cold water to which was added triflouroethanol to 30%. This was cooled at 4° C. for two hours before oxidised and reduced glutathione was added (10:100:1/GSSG:GSH:peptide; GSSG disclosed as SEQ ID NO: 26) then 1 M $NH_4HCO_3$ was added to give a 0.1 M solution at pH 8.1. The oxidised peptides were isolated HPLC.

Circular Dichroism

CD was performed as outlined in the General Materials and Methods section.

NMR of ERP01 and 03

The NMR structure of ERP01 and ERP03 and the Cα–Cβ and Cα–NHα connectivities were determined as outlined in the General Materials and Methods section.

Example 5

Interleukin 4 (IL-4)

IL-4 is a four helix bundle cytokine that is the basis of the allergic response mechanisms in asthma, rhinitis, conjunctivitis and dermatitis. It plays an important role in the induction of immunoglobulins through the turning on of B-cells that produce Igm, IgE and IgG's. IL-4 associates primarily with the IL-4 alpha receptor which accounts for nearly the complete binding affinity. The IL-4 receptor complex then recruits the common γ chain to form the cell signaling heterodimer.

The functional epitope of IL-4 that determines the binding affinity to the receptor a chain has been identified through mutational analysis and from the crystal structure of the recently determined IL-4 and the IL-4Rα complex. (Hage et al., 1999, Cell 97 271) The key binding event involves mainly charged residues from helix A and C of IL-4 particularly Arg88 and Glu9.

The 13 amino acid residues of the binding surface of IL-4 were used as a query for program VECTRIX. In this case the database to be searched contained the structure of GCN4, a 31 residue leucine zipper peptide. The GCN4 molecule was identified by the program VECTRIX as a hit. It matched 8 vectors of IL-4 (RMS 0.39 Å). Upon engineering and synthesising this molecule containing these 8 amino acids, an IL-4 agonist is expected with a potency of Kd 106 μM (Dominques et al., 1999, Nat. Struct. Biol. 6 652).

An additional molecule ZDC was found that matches 10 vectors. Upon synthesising the engineered framework it will be folded and assayed.

Vectrix Results

Number of vectors searched: 13: K77, R81, K84, R85, R88, N89, W91, T13, E9, I5, R53, F82, K12

Total Number of Different Matches at 7 or More

396

Number of Unique Frameworks

30

Number of Different Frameworks Selected (Name:pdb Code: # Vector Matches)

GCN4 peptide: pdb1zta (8)

Protein A fragment (engineered): pdb1zdc: (10)

N.B. No molecule selected in the search matched to Arg53.

Example 6

CD4 GP120

The CD4-GP120 interaction is the primary binding event that allows the Human Immunodeficiency Virus (HIV) to enter a cell. The crystal structure of CD4 has been known for some time (Wang et al., 1 990, Nature 348 411) but a structure of the CD4 and a highly modified GP120 complex was only solved in June 1998 (Kwong et al., 1998, Nature 393 648). It has been known for some time through mutational analysis of CD4 (Fleury et al., 1991, Cell 66 1037) that the key amino acids involved in binding to GP120 reside on a loop (CDR1) involving the residues 41–47 and the key binding residue Arg59.

The Cα–Cβ vectors of these residues were used in a VECTRIX search. Two molecules SCY and PTA (FIG. 14) were identifed as potential matches. Both molecules were optimised using a design procedure as described above.

The biological activity of SCY is consistent with the studies of Vita et al., 1998, Biopolymer 47 93.

Experimental for Example 6

Vectrix Results

Number of vectors searched: 7: K35, S42, F43, R59, D63, Q40, L44.

Total Number of Different Matches

At 4 or more matches. 409

Number of Unique Frameworks

116

Number of Different Frameworks Selected (Name:pdb code: # Vector Matches)

Scorpion neurotoxin: pdb2pta (5)

Scyllatoxin :pdb1scy: (4)

The scy molecule is only selected in the vectrix search if the absolute requirement of a match with Arg59 is removed.

Synthesis of PTACD4 and SCYCD4 Molecules

As described in the General Materials and Methods section.

Oxidation of PTACD4 Molecule

The PTA peptide was oxidised by stirring the peptide overnight in 0.1M $NH_4HCO_3$ pH 8.1. The oxidised peptide (2 forms) was recovered by HPLC. Both folded forms were assayed separately. The oxidation of the peptide in different conditions in the presence of glutathione failed to yield folded peptide.

Oxidation of SCY Molecule

The SCY CD4 molecule was oxidised using 5 mM GSSG (SEQ ID NO: 26) to 0.5 mM GSH in $NaPO_4$ buffer pH 7.4. The oxidised peptide was purified by HPLC.

Biacore Assay

GP120 bound to the Biacore chip through NHS coupling onto a CM-5 Biacore chip. CD4 is then passed over the GP120 surface and the degree of binding assessed through both the on rate $K_{Association}$ and the off rate $k_{Dissociation}$. CD4 is then equilibrated with the inhibitor ligand and passaged over the GP120. Through the BiaCore module the degree to which the PTA or SCY ligand disrupts the binding of CD4 to the chip is assessed.

Example 7

Interleukin 6 (IL-6)

Interleukin 6 (IL-6) is a cytokine that plays an important role in the inflamation cascade, neural development, bone metabolism, hematopoiesis cell proliferation and immune response mechanisms. Interleukin 6 is a 4 helical bundle cytokine that binds to a IL-6 alpha receptor and to a common receptor motif GP130. The IL-6R α subunit does not play a role in intracellular signalling. This is carried out through the ligand dependent dimerisation of the associated GP130 receptor molecule. The full receptor complex is believed to be hexameric with two units each of IL-6, IL-6R and GP130. The pleiotropic effects of IL-6 is thought to come about because of this complex arrangement of the heterotrimeric receptor complex. The interaction sites for both the IL-6Rα and GP130 receptors has been well studied through site specific mutagenisis of both the receptor molecules and the IL-6 molecule. The structure of IL-6 in both solution and crystal forms has been solved and the crystal structure of the GP130 receptor has recently been determined.

The IL-6α receptor binding site on IL-6 (termed Site I) is localised primarily to the end of helix D. Two additional sites Site II and III are responsible for the two different GP130 receptor molecules binding. The two GP130 binding sites are spread over a wide area at the opposite end of the molecule to the IL-6 binding site.

The IL-6 VECTRIX search described herein pertains only to the II-6α receptor interaction. It does not relate to the GP130 receptor interaction or the multi receptor interactions (though the VECTRIX search has been carried out for these two sites II and III as well). No modeling of the IL-6 residues to any of the hit frameworks has been carried out. A few examples of possible framework targets are listed below.

Vectrix Results

Number of vectors searched: 21 Subset1 (Site I) 8 vectors: Subset 2 (Site II and III) 13 vectors.

Number of Different Matches at 8 and Above Matches for Site I

179

Number of Unique Frameworks

29

Number of Different Frameworks Selected (Name:pdb code: # Vector Matches)

Protein A fragment (engineered): pdb1zdc: (9)

Moloney murine leukemia virus fragment: Pdb1mof: (10)

Scyllatoxin: pdb1scy: (8)

Example 8

G-CSF

Granulocyte Colony Stimulating Factor (G-CSF) is part of the class of 4 helical bundle cytokine or growth factors. It is involved in the promotion of cell proliferation and differentiation leading to the production of mature neutrophils. Its ability to replenish these neutrophils in-vivo makes it an attractive drug target. G-CSF functions through receptor dimerisation of the CSF receptor. There has been alanine scanning mutagenisis carried out on G-CSF to identify the key residues involved in receptor recognition. The crystal structure of G-CSF has been available since 1993 (Hill et al., 1993, Proceedings of the National Acadamy of Science USA 90 5167) and the NMR structure since 1994 (Zink et al., 1994, Biochemistry 33 8453).

The VECTRIX search was done with an absolute requirement for a vector matching the critical amino acid Phe 145. However, relatively few hits resulted, presumably due to the restriction of every hit matching the Phe 145 vector. Alterations of this absolute requirement and refinement of the VECTRIX search will lead to a larger number of hits.

Experimental to Example 8

Vectrix Results

Number of vectors searched: 18

Number of Different Matches
338

Number of Unique Frameworks
115

Number of Different Frameworks Selected (Name:pdb Code: # Vector Matches)

Further refinement of the vectrix search is needed before a selection as to probable ligand frameworks.

GENERAL MATERIALS & METHODS

Design

Database searching and all design steps were carried out on either an R10000 or R12000 SGI Octane workstation. Database searching was performed with VECTRIX. Visualisation and peptide mutations and modifications were performed using Software programs from Biosym/MSI of San Diego-InsightII and Biopolymer respectively. Analysis of electrostatic potential character of the molecules was carried out using Biosym/MSI of San Diego-DelPhi, while surface area calculations were performed with Naccess (Hubbard & Thornton, 1993, 'NACCESS', Computer Program, Department of Biochemistry and Molecular Biology, University College London) Molecular mechanics minimisations and molecular dynamics calculations were performed on the mutated frameworks to determine whether the native fold was retained. Programs such as X-SITE (Laskowski et al., 1996 Journal of Molecular Biology, p175–201) were used to add additional functionality to the mutated peptides.

Chemicals and Reagents

Trifluoroacetic acid (TFA) dichloromethane (DCM) dimethylformamide (DMF) and disopropylethylamine (DIEA) were from Auspep (Melbourne Australia). 2-(1H-benzotriazol-1-yl)-1,1,3,3-tetramethyl uronium hexafluorophosphate (HBTU) was from Richelieu Biotechnologies (St. Hyacinth, Quebec, Canada). Acetonitrile was from BDH Laboratory Supplies (Poole, U.K.), Diethyl ether from Fluka Biochemicals (Melbourne) and 2-mercaptoethanol from Sigma (St. Louis Mo., USA). Trifluoroethanol from (Aldrich. Milwaukee, Wis., USA). HF was purchased from Boc Gases (Brisbane, Australia) The following Nα-Boc protected L-amino acids Ala, Gly, Ile, Leu, Phe, Pro, Val, Arg (Tos), Asp (OChx), Asn(Xanth), Glu (OChx), His(DNP), Ser(Bzl), Thr (Bzl), Tyr(2BrZ) were purchased either from NovaBiochem (La Jolla, Calif., USA) or Bachem (Switzerland). MBHA polystyrene resin was purchased from Peptide Institute (Kyoto, Japan).

HPLC Methods

Analytical and preparative HPLC was carried out using a Waters HPLC system comprised of model 600 solvent delivery system 600E controller and model 484 detector. Vydac C18 and C4 columns analytical (4.6×250 mm id) at a flow rate of 1 ml/min and semi preparative (10×250 mm id) at a flow rate of 3 ml/min and preparative (22×250 mm id) at a flow rate of 8 ml/min were used. All peptides were purified using linear gradients of 0.1% aqueous TFA (solvent A), 90% aqueous to acetonitrile 0.09% TFA (solvent B).

Peptide Synthesis

Peptides were synthesized using the rapid manual HBTU in-situ neutralization synthesis techniques (Schnolzer et al., 1992, supra) on a modified ABI 430A peptide synthesizer (Alewood et al., 1997, supra). The peptide was synthesized on a MBHA resin on a 0.2 mmol scale using 0.79 mmol/g NH2 substituted resin. Each amino acid was double coupled using 2 mmol AA 0.48M HBTU (4 ml) and 1 ml DIEA for 10 min each coupling. The Boc group was removed by 2×1 min treatments of TFA with 1 min DMF flow washes of the resin.

At the completion of the synthesis the His(DNP) group, if present in a particular sequence, was removed using 20% mercaptoethanol in 10% DIEA/DMF solution 3×30 min treatments. Peptide resin was cleaved using HF with p-cresol and p-thiocresol (90:8:2) as scavangers at −5 to 0° C. for 2 hrs. If Trp(CHO) is present in a sequence, it is removed by treatment with ethanolamine. The HF was removed in vacuo, the peptides triturated with cold diethyl ether (3×50 ml) the precipitated peptide collected then dissolved in 50% acetonitrile with 0.1% TFA to give the crude peptide. The crude peptide (~80 mg lots) was purified by RPHPLC and fractions collected and analysed by analytical RPHPLC and ESMS. Fractions containing the purified peptide were combined and lyophilised.

Mass spectral data were collected using a Perkin Elmer Sciex (Toronto, Canada) API III Biomolecular Mass Analyzer ion-spray mass spectrometer equipped with an ABI 140B solvent delivery system. Raw data was analyzed using the program MassSpec (Perkin Elmer Sciex). Calculated masses were obtained using the program MacProMass (Sunil Vemuri & Terry Lee, City of Hope, Durate, Calif.).

Ultraviolet Circular Dichroism (CD)

Far UV-CD spectra were recorded using a Jasco 710 CD spectrometer with associated based PC software. CD spectra are presented as a plot of mean molar ellipticity per residue [θ] deg $cm^2$ $dmol^{-1}$ verse wavelength in 0.1 nm increments. The digitised data was ploted using the Kalidagraph program on a Macintosh. All peptide concentrations were determined by quantitative amino acid analysis.

$^1$H NMR Spectroscopy

All NMR experiments were recorded on a Bruker ARX 500 spectrometer equipped with a Z-gradient unit. Peptide concentration was approximately 3 mM in 95% $H_2O$/5% $D_2O$ (T=293K). Spectra recorded included NOESY (Kumar et al., 1980, Biochem. Biophys. Res. Comm. 95 1; Jeener et al., 1979, 71 4546) with a mixing time of 400 millisecond, and TOCSY (Bax & Davis, 1985, 65 355) with a mixing time of 85 millisecond. Spectra were run over 5550 Hz with 4K data points, 512 FIDs, 32–64 scans and a recycle delay of 1 s. The solvent was suppressed using the WATERGATE sequence (Piotto et al., J. Biomol. NMR, 1992, 2 661) Spectra were processed using UXNMR. FIDS were multiplied by a polynomial function and apodised using a 90° shifted sine-bell function in both dimensions prior to Fourier transformation. Baseline correction using a $5^{th}$ order polynomial was applied and chemical shift values were referenced externally to DSS at 0.00 ppm. The random coil H chemical shift values of Wishart et al., 1995, J. Biomol. NMR 6 135, were used. Spectra were assigned using the methods of Wüthrich et al., 1986, NMR of Proteins and Nucleic Acids. Wiley-Interscience NY.

Growth Hormone Proliferation Assay

BaF-B03 cells (a pro B cell line) that stably express the human Growth Hormone Receptor (hGHR) are used in this assay since they are able to elicit a GH-specific response at concentrations as low as 0.1 ng/mL hGH (4.54 pM). These cells also endogenously express the IL3 receptor and require IL3 or GM-CSF to survive in culture. The assay is based on that of Mossman, 1983, J. Immunol. Meth. 65 55, and involves the following procedure:—

(i) culture cells in RPMI-1640 medium supplemented with 10% (v/v) foetal bovine serum (FBS) and 100 units/mL IL3 under 5% $CO_2$ at 37° C. Allow the culture to reach mid-log growth phase;

(ii) centrifuge cells at 500×g and wash with PBS to remove IL3 from the culture medium. Repeat the centrifugation and resuspend in 1 mL of RPMI-1640 plus 0.5% (v/v) FBS. Count cells and dilute to a concentration of $8\times10^5$ cells/mL in same media;

(iii) from a constantly stirred suspension, add 50 μL of cells to each well of two 96 well plates;

(iv) prepare stock solutions of the mimetic to be tested at various concentrations such that the final concentration ranges from 100 nM to 100 μM made up in 0.5% FBS media (final volume is 150 μL, therefore stocks should be 3 times final concentration required). Add 50 μL of these solutions to cells in sextuplicate (i.e. A1 to A6 are identical etc.);

(v) prepare a stock solution (3 times) of hGH such that the final concentration is 0.5 ng/mL and add 50 mL to each well of one plate. Include one row as a negative control with no cytokine;

(vi) prepare a stock solution (3 times) of IL-3 such that the final concentration is 50 units/mL and add 50 μL to each well of the other plate. Include one row as a negative control with no cytokine;

(vii) incubate plates with no lids (to prevent uneven evaporation rates) in a vented humidified box under the abovementioned incubation conditions. Allow incubation to continue for 24 hrs;

(viii) add 50 μL of 4 mg/mL MTT (3-[4,5-dimethylthiazol-2-yl]-2,5-diphenyltetrazolium bromide) to each well and incubate for a further 3 hrs;

(ix) to stop assay, remove from incubator and lyse cells by adding 120 μL of isopropanol and triturating for several seconds per well or until cells are clearly lysed. Allow plate to rest in the dark for 5 minutes before reading;

(x) read plate at 595 nm on a microplate reader. Values obtained are directly proportional to cell number (as measured by mitochondrial dehydrogenase levels).

CONCLUSIONS

These studies have shown that by engineering small, cysteine-rich proteins, a stable mimetic with high bioavailability can be made with desired biological characteristics, in this case the ability to antagonize the biological action of hGH. Furthermore, the database searching strategy of the present invention has shown that suitable "frameworks" for engineering mimetics can be identified according to aspects of structure which are shared with a sample protein that possesses a function of interest. The framework so identified will advantageously have increased stability compared to the sample protein. Finally, frameworks identified by the method of the invention may be suitable for further amino acid sequence modification so as to impart a function of the sample protein, or a function antagonistic thereto.

The present invention therefore provides a new strategy for the engineering of proteins, which strategy is particularly applicable to the engineering of mimetics which may constitute the next generation of therapeutics.

It will be understood by the skilled person that the invention is not limited to the particular embodiments described in detail herein, but also includes other embodiments consistent with the broad spririt and scope of the invention.

TABLE 1

An example of a query file which define the query Cα-Cβ vectors, the tolerance for each query atom and the definition of subset

| | | | | | | | | |
|---|---|---|---|---|---|---|---|---|
| ATOM | 344 | Cα | LYS A 41 | 54.743 | 11.420 | 29.859 | 0.50 | 33.97 |
| ATOM | 347 | Cβ | LYS A 41 | 53.280 | 11.410 | 30.298 | 0.50 | 36.33 |
| ATOM | 382 | Cα | LEU A 45 | 58.116 | 17.055 | 29.052 | 0.50 | 30.56 |
| ATOM | 385 | Cβ | LEU A 45 | 56.870 | 17.340 | 29.906 | 0.50 | 27.80 |
| ATOM | 274 | Cα | GLU A 119 | 43.893 | 28.064 | 0.887 | 0.50 | 0.00 |
| ATOM | 277 | Cβ | GLU A 119 | 43.099 | 27.286 | −0.137 | 0.50 | 0.00 |
| ATOM | 296 | Cα | THR A 123 | 41.789 | 33.792 | 1.008 | 0.50 | 0.00 |
| ATOM | 299 | Cβ | THR A 123 | 40.586 | 32.811 | 0.784 | 0.50 | 0.00 |

Subset 1, 3, 4.
Subset 2.

TABLE 2

| | Blood serum stability test results | | |
|---|---|---|---|
| | 0 hr | 1 hr | 24 hrs |
| Control peptide | partially digested after 3 mins | fully digested | |
| SCY01 | stable | stable | stable |

TABLE 3

| | Enzyme stability test results | |
|---|---|---|
| | Control peptide | SCY01 |
| trypsin | Digested in 1 hr | Stable over 18 hrs |
| α-chymotrypsin | Digested in 1 hr | Stable over 18 hrs |
| pepsin | Digested in 1 hr | Stable over 18 hrs |

Scheme A: An overview of the functioning of the program Vectrix.

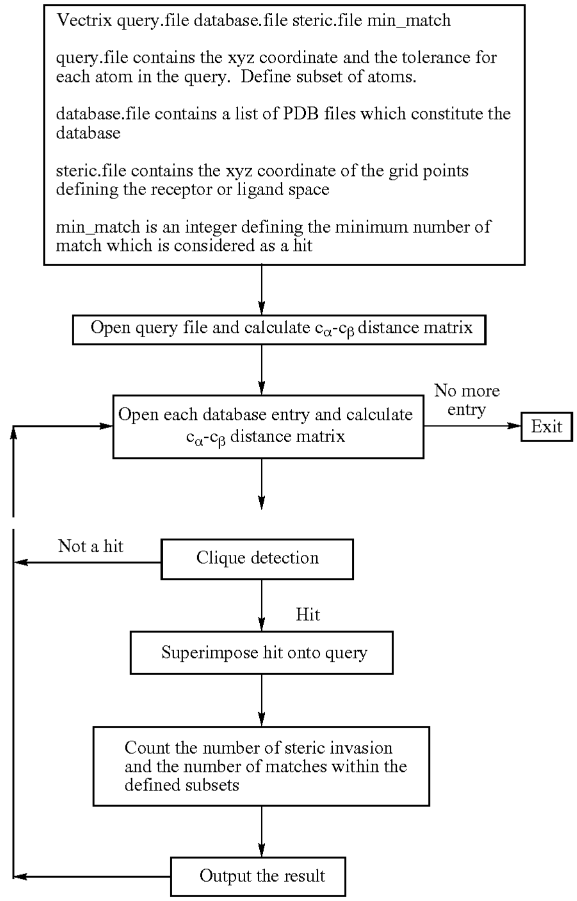

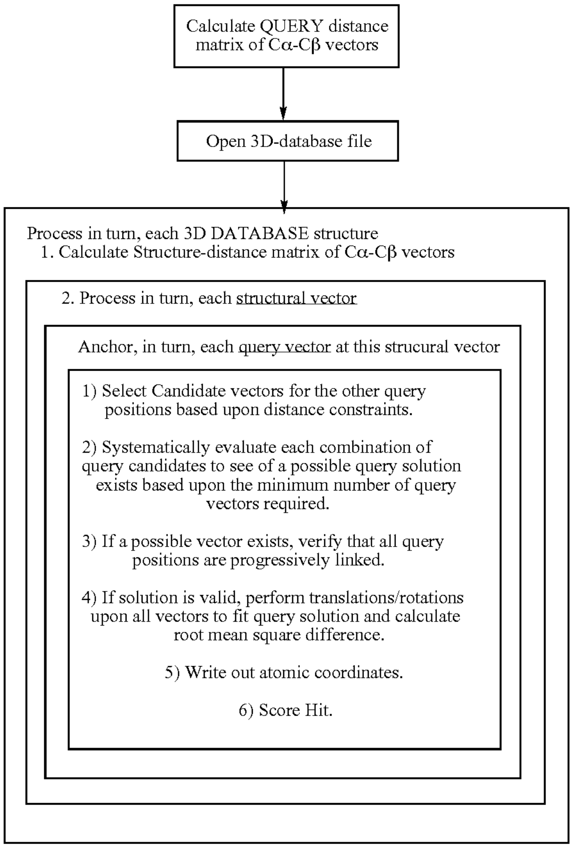

Automatic weekly job

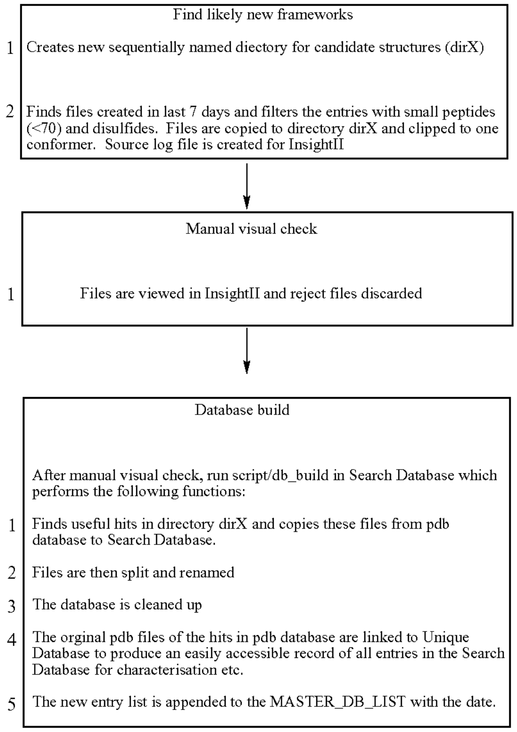

Scheme D

1) Framework hit mutated to sample molecule residues: Using the Biopolymer module of InsightII, the residues matching the sample molecule are mutated to the residue type of the sample molecule. Using the Search_compare module of InsightII, the sidechains of the mutated residues of the framework hit are flexibly fitted to the sidechains of their corresponding sample molecule residues to produce a theoretical 'Bioactive conformation'. A bump-check with the receptor is performed to identify unmutated sidechain steric clashes with the receptor. Investigate mimicking unmatched functional residues of sample molecule with unnatural amino acids.

Passed ↓ Failed → Discard or rectify (a)

2) C nformational stability of theoretical'bioactive conformation': The 'bioactive conformation'from above is minimised in a forcefield. The rmsd of the backbone atoms ofthe minmised mutated framework hit from the minimised unmutated framework hit is calculated. If the rmsd<2.0 A, the conformation is considered accessible.

Passed ↓ Failed → Discard or rectify (b)

3) Stability of fold: The mutated framework hit and the native framework hit are subject to molecular dynamics at 300K. The rmsd of minimised trajectory intermediates from the original conformer in each dynamics run are plotted. Unless there is a significantly greater drift in rsmd of the mutated relative to native framework hit, the fold is considered stable.

-continued

Passed ↓ Failed → Discard or rectify (b)

4) Electrostatic similarity to target: Electrostatic isocontour surfaces are generated for both mutated framework hit and sample molecule and compared for similarity. Electrostatic fields are mapped onto solvent accessible surface of mutated framework hit and sample molecule to compare electrostatic properties at the contact surface Passed ↓ Failed → Discard of rectify (c)

5) Synthesise

Rectify (a): If there are steric clashes, consider the most conserved mutation that removes the bump.

Rectify (b): If the theoretical 'Bioactive conformation' is not stable, check the Ramachandran plot of the hit for residues in disallowed regions. Consider stabilizing structure with unatural amino acids eg alpha-amino isobutyric acid in alpha helix motifs.

What is claimed is:

1. A method of protein engineering including the steps of:—

(i) creating a computer database which includes a plurality of entries, each said entry corresponding to a description of a location and orientation in 3D space of side chains of amino acid residues of a framework protein which comprises 70 amino acids or less and has 1–11 disulfide bonds, wherein the location and orientation of each side chain is represented by a $C_\alpha$–$C_\beta$ vector;

(ii) creating a query corresponding to a description of a location and orientation in 3D space of each side chain of two or more amino acid residues of a sample protein which are required for a function of said sample protein, wherein the location and orientation of each side chain is represented by a $C_\alpha$–$C_\beta$ vector;

(iii) searching said database with said query to thereby identify one or more hits wherein at least one of said hits corresponds to a respective said framework protein which has 3D structural similarity to said sample protein;

(iv) identifying the amino acid residue(s) of the framework protein hit identified at step (iii) that structurally correspond(s) to each of the two or more amino acid residues of said sample protein used to create the query at step (ii);

(v) determining which amino acid residue(s) identified at step (iv) is/are to be substituted by another amino acid to impart a particular property, characteristic or function to the framework protein identified as a hit; and (vi) modifying said framework protein which corresponds to a hit, by substituting at least one amino acid residue thereof determined at step (v) with another amino acid to thereby create an engineered framework protein having the particular property, characteristic or function.

2. The method of claim 1, wherein said another amino acid used for substitution at step (v) is at least one of the two or more amino acid residues used to create the query at step (ii).

3. The method of claim 1 wherein the two or more amino acid residues of said sample protein used to create the query at step (ii) are non-contiguous in primary sequence.

4. The method of claim 1, further including the step of determining that the engineered framework protein has greater stability than said sample protein.

5. The method of claim 1, further including the step of determining that the engineered framework protein has increased structural similarity with said sample protein when compared to the structural similarity between said sample protein and said framework protein identified as a hit.

6. The method of claim 1, further including the step of determining that the engineered framework protein exhibits a function which is either similar to, or inhibitory of, a function of said sample protein.

7. The method of claim 1, wherein the sample protein is a cytokine.

8. The method of claim 7, wherein the cytokine is selected from the group consisting of GH, IL-4, IL-6 and G-CSF.

9. The method of claim 1 wherein said query of step (ii) is a single query.

10. The method of claim 1, wherein at step (v) at least one amino acid residue in addition to the amino acid residue(s) identified at step (iv) is identified for substitution by another amino acid to impart a particular property, characteristic or function to the framework protein identified as a hit.

11. The method of claim 1 wherein the amino acids of the framework protein substituted at step (vi) are non-contiguous in primary sequence.

12. The method of claim 1, wherein at step (iii) the hits are ranked according to structural similarity with said sample protein.

13. The method of claim 1, wherein searching at step (iii) includes:

(a) identification of said hits by clique detection;

(b) filtering of said hits identified at step (a) by comparing each said hit with said query to thereby select one or more of said hits having 3D structural similarity to said sample protein.

* * * * *